US011503918B2

(12) United States Patent
Tsern et al.

(10) Patent No.: US 11,503,918 B2
(45) Date of Patent: Nov. 22, 2022

(54) SLEEP PHASE DEPENDENT TEMPERATURE CONTROL AND LEARNING METHODS TO OPTIMIZE SLEEP QUALITY

(71) Applicants: Ely Tsern, Los Altos, CA (US); Matthew Walker, Berkeley, CA (US); Jonathan Farringdon, Pittsburgh, PA (US)

(72) Inventors: Ely Tsern, Los Altos, CA (US); Matthew Walker, Berkeley, CA (US); Jonathan Farringdon, Pittsburgh, PA (US)

(73) Assignee: Bryte, Inc., Los Altos, CA (US)

( * ) Notice: Subject to any disclaimer, the term of this patent is extended or adjusted under 35 U.S.C. 154(b) by 704 days.

(21) Appl. No.: 16/401,108

(22) Filed: May 1, 2019

(65) Prior Publication Data
US 2019/0335913 A1 Nov. 7, 2019

Related U.S. Application Data

(60) Provisional application No. 62/665,278, filed on May 1, 2018.

(51) Int. Cl.
*A47C 21/04* (2006.01)
*G05B 13/02* (2006.01)
(Continued)

(52) U.S. Cl.
CPC ............. *A47C 21/04* (2013.01); *A61M 21/02* (2013.01); *G05B 13/0265* (2013.01);
(Continued)

(58) Field of Classification Search
CPC .................. A47C 21/04; A61M 21/02; A61M 2021/0066; A61M 2021/0083;
(Continued)

(56) References Cited

U.S. PATENT DOCUMENTS 7,524,279 B2 4/2009 Auphan
7,967,739 B2 6/2011 Auphan
(Continued)

FOREIGN PATENT DOCUMENTS

CN 101035587 A 9/2007
CN 103945802 A 7/2014
(Continued)

OTHER PUBLICATIONS

International Search Report on related PCT Application No. PCT/US2019/030293 from International Searching Authority (KIPO) dated Aug. 9, 2019.
(Continued)

*Primary Examiner* — Hai Phan
*Assistant Examiner* — Anthony D Afrifa-Kyei
(74) *Attorney, Agent, or Firm* — KOS IP Law LLP

(57) ABSTRACT

A bed includes components to control temperature of a sleep surface, for example based on time and historical usage patterns by a user. In some embodiments the temperature of the sleep surface is controlled based on information indicating a sleep state of the user. In some embodiments the temperature is dynamically adjusted so to achieve particular sleep states and/or sleep patterns for the user. In some embodiments the temperature and timing of temperature adjustments is iteratively adjusted over multiple sleep sessions so to achieve improvements in sleep states and/or sleep quality for the user.

29 Claims, 13 Drawing Sheets

(51) Int. Cl.
  *G05D 23/19* (2006.01)
  *A61M 21/02* (2006.01)
  *A61B 5/00* (2006.01)
  *A61B 5/11* (2006.01)

(52) U.S. Cl.
  CPC ........ *G05D 23/1902* (2013.01); *A61B 5/1113* (2013.01); *A61B 5/4809* (2013.01); *A61B 5/4812* (2013.01)

(58) Field of Classification Search
  CPC .. A61M 2205/3368; A61M 2205/3569; A61M 2205/3592; G05B 13/0265; G05D 23/1902; A61B 5/1113; A61B 5/4809; A61B 5/4812; A61F 7/00; A61F 7/0085; A61F 7/0097; A61F 7/08; A61F 2007/0054; A61F 2007/0076; A61F 2007/0086; A61F 2007/0093; A61F 2007/0295; A61F 2007/0296
  See application file for complete search history.

(56) References Cited

U.S. PATENT DOCUMENTS

| | | |
|---|---|---|
| 8,161,826 B1 | 4/2012 | Taylor |
| 8,533,879 B1 | 9/2013 | Taylor |
| 8,661,915 B2 | 3/2014 | Taylor |
| 8,690,751 B2 | 4/2014 | Auphan |
| 8,800,386 B2 | 8/2014 | Taylor |
| 9,642,470 B2 | 5/2017 | Taylor |
| 10,744,390 B1 | 8/2020 | Kahn et al. |
| 10,945,659 B1 | 3/2021 | Kahn et al. |
| 2015/0351556 A1 | 12/2015 | Franceschetti et al. |
| 2016/0136385 A1* | 5/2016 | Scorcioni ............. A61B 5/4812 600/26 |
| 2016/0361515 A1 | 12/2016 | Jung et al. |

FOREIGN PATENT DOCUMENTS

| | | |
|---|---|---|
| CN | 105096561 A | 11/2015 |
| CN | 105592777 A | 5/2016 |
| CN | 107635461 A | 1/2018 |
| JP | 2003-010230 A | 1/2003 |
| JP | 2014-042773 A | 3/2014 |
| JP | 2016209013 A | 12/2016 |
| KR | 2017-0095649 A | 8/2017 |
| WO | WO 2018-023135 A1 | 2/2018 |

OTHER PUBLICATIONS

Written Opinion on related PCT Application No. PCT/US2019/030293 from International Searching Authority (KIPO) dated Aug. 9, 2019.

Shen, Tsu-Yu et al., "Comparison of Sleep Quality and Thermal Comfort for Innovative Mattress Design", Procedia Manufacturing, 2015, vol. 3, pp. 5874-5880.

Extended European Search Report on related European Patent Application No. EP19796214.5 from the European Patent Office (EPO) dated May 21, 2021.

* cited by examiner

SLEEP PHASE DEPENDENT TEMPERATURE CONTROL AND LEARNING METHODS TO OPTIMIZE SLEEP QUALITY

CROSS REFERENCE TO RELATED APPLICATION

This application claims the benefit of the filing date of U.S. Provisional Patent Application No. 62/665,278, filed on May 1, 2018, the disclosure of which is incorporated by reference herein.

BACKGROUND OF THE INVENTION

The present invention relates generally to sleep environments, and more particularly to temperature control of sleep environments.

Sleep is a universal need for people. Sleep provides many physiological benefits, and a sound night's sleep is often desired by many. Unfortunately, some may not obtain good quality sleep, even when sufficient time and preparation for sleep is available.

BRIEF SUMMARY OF THE INVENTION

Some aspects provide for setting, to a first temperature, at least a portion of a sleep surface prior to a time a user is expected to sleep on the sleep surface; receiving an indication that a user is asleep on the sleep surface; in response to receiving the indication the user is asleep on the sleep surface, setting the at least the portion of the sleep surface to a second temperature, the second temperature lower than the first temperature, for a period of time. In some embodiments the period of time is a first period of sleep of the user. In some embodiments the first period of sleep is a first two sleep cycles of the user. In some embodiments the first period of sleep is a first three sleep cycles of the user.

In some embodiments the first period of time is indicated by a predetermined period of time. In some embodiments the first period of time is indicated by processing of biometric sensors, the processing of biometric sensors indicating sleep stages of the user.

In some embodiments the at least the portion of the sleep surface is set to the first and second temperatures by heating or cooling air provided to the sleep surface. In some embodiments the heating or cooling of air is performed using a thermoelectric device. In some embodiments the thermoelectric device is a Peltier device. In some embodiments the at least the portion of the sleep surface is set to the first and second temperatures using a resistive heating device. In some embodiments the at least the portion of the sleep surface is set to the first and second temperatures using both a resistive heating device and a thermoelectric device.

In some embodiments the indication that the user is asleep on the sleep surface comprises an indication that a predetermined time of day has been reached. In some embodiments the indication that the user is asleep on the sleep surface comprises a lapse of time after an indication that the user is on the sleep surface. In some embodiments the indication that the user is on the sleep surface is provided by a pressure sensor configured to sense pressure on the sleep surface.

In some embodiments the indication that the user is asleep on the sleep surface is an indication provided through processing of information from biometric sensors, the processing of information from biometric sensors indicating sleep stages of the user.

Some aspects of some embodiments further comprise storing an indication of time for which the user is in a deep non-rapid eye movement (non-REM) sleep stage, or a slow wave sleep stage, in a period of sleep during a period the at least the portion of the sleep surface is set to the second temperature; subsequently setting the at least the portion of the sleep surface to a different temperature, the different temperature lower than the second temperature, for a period of time indicated as two sleep cycles of the user; determining if an indication of time for which the user is in a deep non-rapid eye movement (non-REM) sleep stage in a period of sleep during a period the at least the portion of the sleep surface is set to the different temperature is greater than that for the second temperature; and setting the second temperature to the different temperature if so. In some embodiments sleep stages of the user are determined through processing of information from biometric sensors.

Some aspects of some embodiments further comprise setting the at least the portion of the sleep surface to a third temperature at a third time, while the user is asleep and at a time prior to the user awakening. In embodiments the third time is a predetermined time. In some embodiments the predetermined time is a time which is a predetermined duration before the user is expected to awake. Some aspects of some embodiments further comprise determining that a sleep stage of the user at a time immediately prior to user awakening is not a lightest sleep stage, and changing the third time and/or changing the third temperature in response to determining that the sleep stage of the user at the time immediately prior to user awakening is not the lightest sleep stage. In some embodiments the sleep stage of the user immediately prior to the time of awakening is determined through processing of information from biometric sensors. In some embodiments a time of user awakening is determined using information from a motion and/or pressure sensor. In some embodiments a time of user awakening is determined based on an alarm time for the user. In some embodiments, the third temperature is achieved by turning off the temperature control of the sleep surface and letting the body naturally regulate the sleep surface temperature.

Some aspects of some embodiments provide a bed with an adjustable temperature sleep surface, and a controller configured to monitor time of day and to command adjustment of temperature of the sleep surface based on time of day. In some embodiments the controller is additionally or instead configured to receive information from pressure and/or biometric sensors and to determine a sleep stage of a user based on information from the biometric sensors, and to command adjustment of temperature of the sleep surface based on information regarding the sleep stage of the user. In some embodiments the temperature of the sleep surface is adjustable using a resistive heater. In some embodiments the temperature of the sleep surface is adjustable using forced air or other fluids heating and/or cooling. In some embodiments air of a forced air heating and/or cooling system of the bed is performed using, at least in part, a thermoelectric device. In some embodiments the thermoelectric device is a Peltier device. In some embodiments the controller is configured to set the temperature of the sleep surface of the bed to be at a first temperature at a time the user is expected to lie on the sleep surface, and to set the temperature of the sleep surface of the bed to be at a second temperature at a time the user is expected to be asleep on the sleep surface, the second temperature lower than the first temperature. In some embodiments the controller is further configured to cease setting the temperature of the sleep surface of the bed to the second temperature at a time the user is expected to have completed a number of sleep cycles. In some embodiments the number of sleep cycles is two sleep cycles. In some embodiments the number of sleep cycles is three sleep cycles. In some embodiments the time the user is expected to lie on the sleep surface is determined based on time of day. In some embodiments the time the user is expected to lie on the sleep surface is determined based on information from a pressure and/or motion sensor. In some embodiments the time the user is expected to be asleep on the sleep surface is determined based on time of day. In some embodiments the time the user is expected to be asleep on the sleep surface is determined based on information from biometric sensors. In some embodiments the time the user is expected to have completed the number of sleep cycles is determined based on time of day. In some embodiments the time the user is expected to have completed the number of sleep cycles is determined based on information from biometric sensors. In some embodiments the time the user is expected to have completed the number of sleep cycles is predetermined based on historical information from biometric sensors.

In some embodiments the controller is further configured, in some embodiments iteratively, to determine a period of time during which the user experienced deep non-REM sleep stages during the first two sleep cycles, to command the temperature of the sleep surface during at least some subsequent occurrences of the number of sleep cycles to a temperature different than the second temperature, to determine if the user experienced deep non-REM sleep stages during the at least some subsequent occurrences of the first two sleep cycles with the sleep surface temperature different than the second temperature, and to change a value for the second temperature to the temperature different than the second temperature if the user experienced a longer period of time in deep non-REM sleep stages during the subsequent occurrences of the first two sleep cycles with the temperature different than the second temperature.

Some embodiments provide a method for conditioning a sleep environment, comprising: receiving an indication that a user is on a sleep surface; and after receiving the indication that the user is on the sleep surface, setting at least a portion of the sleep surface to a first temperature for a first period of time, the first period of time being less than a total period of time the user is expected to be asleep on the sleep surface during a sleep session.

In some embodiments the setting of the at least the portion of the sleep surface occurs after receiving an indication that the user is asleep on the sleep surface. In some embodiments the first temperature is lower than a stable temperature of the sleep surface after the user is on the sleep surface and before the at least a portion of the sleep surface is set to the first temperature. In some embodiments the first temperature is lower than a temperature at the sleep surface at a time of receipt of the indication that the user is asleep on the sleep surface. In some embodiments the indication that the user is asleep on the sleep surface is based on information from biometric sensors. In some embodiments the indication that the user is asleep on the sleep surface comprises a period of time after receiving an indication that the user is on the sleep surface. In some embodiments the indication that the user is on the sleep surface is provided by a pressure sensor indicating pressure on the sleep surface. In some embodiments the first period of time is a first sleep cycle of the user. In some embodiments the first period of time is a first two sleep cycles of the user. In some embodiments the first period of time is a first three sleep cycles of the user. In some embodiments the first period of time is a predetermined period of time. Some embodiments further comprise determining sleep stages of the user through processing of information from biometric sensors. In some embodiments the first period of time concludes at a time the determined sleep stage of the user is a REM-dominant sleep stage. Some embodiments further comprise: determining an amount of time the user experienced slow wave sleep stages during the first period of time; for a subsequent sleep session, receiving a further indication that that the user is asleep on the sleep surface, and, after receiving the further indication that the user is asleep on the sleep surface, setting the portion of the sleep surface to a second temperature for the first period of time during the subsequent sleep session; determining an amount of time the user experienced slow wave sleep stages during the first period of time of the subsequent sleep session; determining that amount of time the user experienced slow wave sleep stages during the first period of time of the subsequent sleep session is longer than the amount of time the user experienced slow wave sleep stages during the first period of time; and in response to determining that the amount of time the user experienced slow wave sleep stages during the first period of time of the subsequent sleep session is longer than the amount of time the user experienced slow wave sleep stages during the first period of time, setting the portion of the sleep surface to the second temperature during the first period of time during further subsequent sleep sessions. In some embodiments the first temperature is based on a stored first value indicating the first temperature, and with the some embodiments further comprising: storing an indication of amount of time for which the user is in a slow wave sleep stage during the first period of time; subsequently setting the portion of the sleep surface to a different temperature, for at least a second period of time; determining that an amount of time the user is in a slow wave sleep stage in the second period of time with the sleep surface set to the different temperature is greater than the amount of time the user is in the slow wave sleep stage during the first period of time; and in response to the determination regarding the amounts of time the user is in the slow wave sleep stage, setting the first value to a value reflecting the different temperature. In some embodiments the subsequently setting the portion of the sleep surface to the different temperature occurs during a subsequent sleep session to the setting the portion of the sleep surface to the first temperature. Some embodiments further comprise, for a time after setting the first value to the value reflecting the different temperature, receiving a further indication that that the user is asleep on the sleep surface, and, after receiving the further indication that the user is asleep on the sleep surface, setting the portion of the sleep surface to the different temperature. In some embodiments the different temperature is up to 5 degrees Fahrenheit below the first temperature. Some embodiments further comprise setting the portion of the sleep surface to a third temperature prior to a time the user is expected to sleep on the sleep surface. In some embodiments the third temperature is greater than the first temperature. In some embodiments the portion of the sleep surface is set to the first temperature by heating or cooling the sleep surface. In some embodiments the heating or cooling of the sleep surface is performed using a thermoelectric device. Some embodiments further comprise setting the portion of the sleep surface to a fourth temperature at a time the user is asleep. In some embodiments the portion of the sleep surface is set to the fourth temperature a predetermined time before the user is expected to awake. In some embodiments the predetermined time before the user is expected to awake is longer than the time is takes for the sleep surface to reach the fourth temperature, such that the fourth temperature is reached before the user is expected to awake. Some embodiments further comprise: determining that a sleep stage of the user was not a lightest sleep stage immediately prior to awakening; and in response to the determination, setting the predetermined time to an earlier time for subsequent sleep sessions. Some embodiments further comprise: determining that a sleep stage of the user was not a lightest sleep stage immediately prior to awakening; and in response to the determination, setting the fourth temperature with a temperature higher than the fourth temperature for subsequent sleep sessions. Some embodiments further comprise: for a subsequent sleep session, setting the portion of the sleep surface to a different temperature instead of the fourth temperature at the predetermined time before the user is expected to awake from the subsequent sleep session; determining that the user awakes closer to the expected wake time for the subsequent sleep session than for the prior sleep session; and in response to the determination, setting the portion of the sleep surface to the different temperature at the predetermined times before the user is expected to awake for further subsequent sleep sessions. Some embodiments further comprise: for a subsequent sleep session, setting the portion of the sleep surface to the fourth temperature at a time different than the predetermined time before the user is expected to awake from the subsequent sleep session; determining that the user awakes closer to the expected wake time for the subsequent sleep session than for the prior sleep session; and in response to the determination, setting the portion of the sleep surface to the fourth temperature at the time different than the predetermined time before the user is expected to awake for further subsequent sleep sessions. In some embodiments the sleep stage of the user is determined using biometric sensors. In some embodiments the portion of the sleep surface is set to the different temperatures over multiple sleep sessions, and the amount of time the user is in a slow wave sleep stage is determined as a statistically calculated value.

Some embodiments provide a bed, comprising: an adjustable temperature sleep surface; and a controller configured to command adjustment of temperature of the sleep surface based on information regarding a user of the sleep surface.

In some embodiments the information regarding the user of the sleep surface comprises time of day information and information regarding time of expected sleep of the user. In some embodiments the controller is configured to command adjustment of temperature of the sleep surface to be a first temperature at a time of day of expected sleep of the user and to cease commanding adjustment of temperature of the sleep surface to be the first temperature a predetermined amount of time after the time of day of expected sleep of the user. In some embodiments the predetermined amount of time is an amount of time in which the user is expected to have complete a predetermined number of sleep cycles. In some embodiments the predetermined number of sleep cycles is two sleep cycles. In some embodiments the predetermined number of sleep cycles is three sleep cycles. In some embodiments the controller is configured to command adjustment of temperature of the sleep surface to a second temperature prior to the time of day of expected sleep of the user. In some embodiments the second temperature is higher than the first temperature. In some embodiments the information regarding the user of the sleep surface comprises a sleep stage of the user. Some embodiments further comprise biometric sensors coupled to the controller, and wherein the controller is further configured to determine sleep stages of the user. In some embodiments the controller is configured to command adjustment of temperature of the sleep surface to a first temperature based on a sleep stage of the user indicating that the user is asleep. In some embodiments the controller is configured to cease commanding adjustment of the temperature of the sleep surface to the first temperature after the user has completed a predetermined time period. In some embodiments the predetermined time period is at least a number of sleep cycles, based on determined sleep stages of the user. In some embodiments the predetermined number of sleep cycles is three sleep cycles. In some embodiments the predetermined number of sleep cycles is two sleep cycles. In some embodiments the controller is configured: to determine the amount of time during which the user experienced slow wave sleep stages during the predetermined time period, to command the temperature of the sleep surface during the predetermined time period for a subsequent sleep session to a temperature different than the first temperature, to determine the amount of time during which the user experienced slow wave sleep stages during the predetermined time period with the sleep surface temperature different than the first temperature, and to change a value for the first temperature to the temperature different than the first temperature if the user experienced a longer period of time in slow wave sleep stages during the predetermined time period with the temperature different than the first temperature. In some embodiments the controller is configured: to determine the amount of time during which the user experienced slow wave sleep stages during the predetermined time period, to receive from a remote server a temperature value different than the first temperature, to command the temperature of the sleep surface during the predetermined time period for a subsequent sleep session to the temperature different than the first temperature, to determine the amount of time during which the user experienced slow wave sleep stages during the predetermined time period with the sleep surface temperature different than the first temperature, to provide information of the amounts of time to the remote server, and to receive a new value for use as the first temperature from the remote server. In some embodiments the controller is configured to, iteratively: determine a period of time during which the user experienced slow wave sleep stages, command the temperature of the sleep surface during the predetermined time period for at least one subsequent sleep session to a temperature different than the first temperature, determine if the user experienced a longer period of time at slow wave sleep stages during the at least one subsequent sleep session with the sleep surface temperature different than the first temperature, and change a value for the first temperature to the temperature different than the first temperature if the user experienced a longer period of time in slow wave sleep stages during the at least one subsequent sleep session with the temperature different than the first temperature. Some embodiments further comprise a thermoelectric device coupled to the controller, the thermoelectric device configured for heating or cooling air or fluid to be provided to the adjustable temperature sleep surface. In some embodiments the controller is further configured to command adjustment of a room temperature for a room including the bed in conjunction with commanding adjustment of temperature of the sleep surface. Some embodiments further comprise activating a light when the user is expected to awake.

These and other aspects of the invention are more fully comprehended upon review of this disclosure.

DETAILED DESCRIPTION

Figure 1:
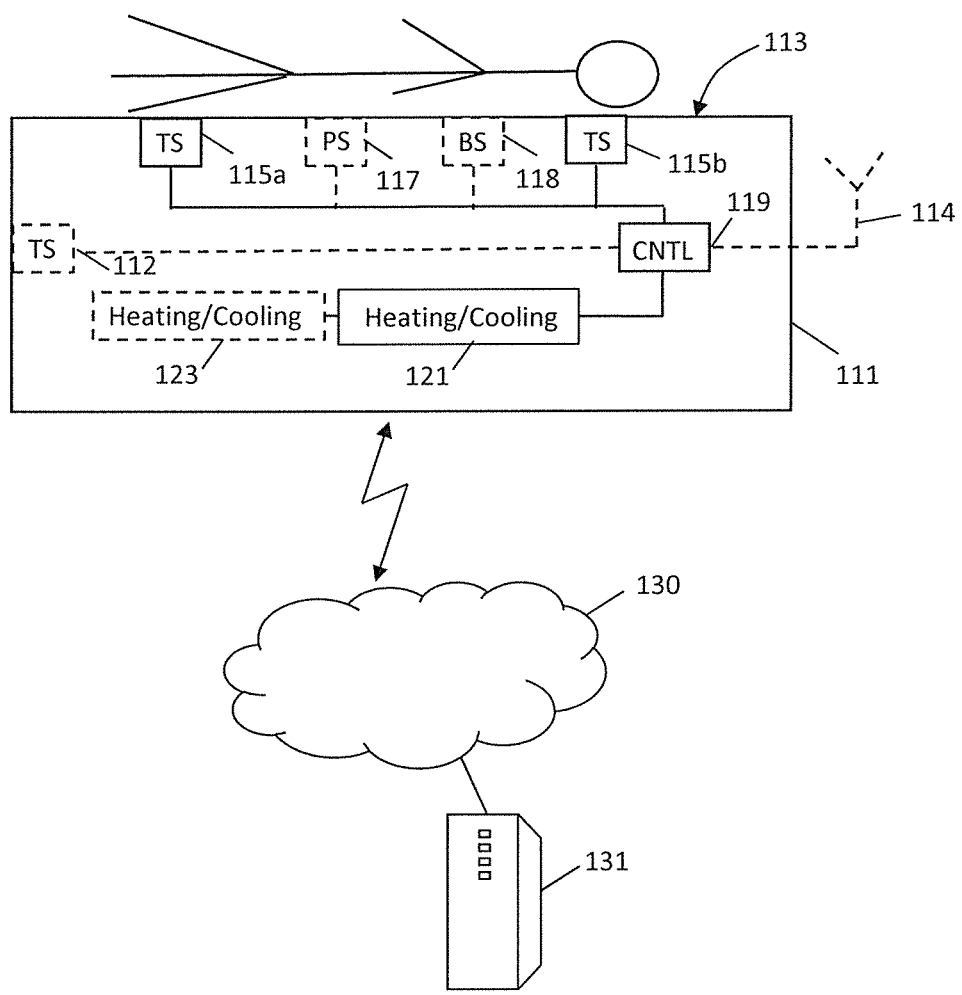
FIG. 1 is a semi-block diagram of a bed in accordance with aspects of the invention.

FIG. 1 is a semi-block diagram of a bed 111 in accordance with aspects of the invention. The bed of FIG. 1 includes a sleep surface 113 as an upper surface. In various embodiments, the sleep surface may be a top surface of a mattress, and in some embodiments the mattress, which itself may be comprised of multiple parts (separable or inseparable) may sit on top of a foundation, with the mattress and foundation considered the bed. In various embodiments, however, the bed may include other parts, and in some embodiments the various parts may be combined into one or more separable or non-separable items. The bed of FIG. 1 may be generally rectangular parallelepiped in form, although other forms may instead be used, and in various embodiments may house a variety of components and materials and be comprised of multiple separable components and/or layers. Generally, a user, or multiple users depending on the bed, sleeps on the sleep surface.

The bed of FIG. 1 includes a heating/cooling component 121. The heating/cooling component is for adjusting temperature of the sleep surface. In some embodiments the heating/cooling component comprises a thermoelectric device, for example a Peltier device. In some embodiments the heating/cooling device comprises a heat pump. In some embodiments, the heating/cooling component may just be a heating component, for example a resistive heater, which in some embodiments may be adjacent or part of the sleep surface. In some embodiments, the heating/cooling component may just be a cooling component, for example an air conditioning device, which in some embodiments may be adjacent or part of the sleep surface. In some embodiments, the heating and/or cooling system includes combinations of heating and/or cooling devices. In the embodiment of FIG. 1 the heating/cooling component is illustrated within the bed, away from the sleep surface. In such embodiments, passageways allowing for thermal transfer between the heating/cooling component and the sleep surface may be provided. For example, in some embodiments, airway passageways are provided between the heating/cooling component and the sleep surface, and some embodiments include other components, for example one or more fans, to assist in conducting heat towards or away from the sleep surface. In some embodiments, where other fluids, for example liquids or fluids that may change between a gaseous and liquid state during use, may be used to control the temperature of the sleep surface, other fluid pathway structures, such as tubes, may be used to move fluids between the active heating and/or cooling component and the sleep surface. Collectively, in some embodiments the temperature control system can include heating and/or heating/cooling components and other fluid (including gaseous fluids) control components, such as fans. The bed may also include a second heating/cooling component 123. The use of a second heating/cooling component may be desirable, for example, in providing differentiation in temperature between different portions of the sleep surface, for example for different sides of the bed used by different users for sleep in a bed normally used by two people or for different regions of the body for a given sleeper. In other embodiments vents or other devices or structures instead or in addition may be used to vary temperature across the sleep surface.

The heating/cooling components are generally under the control of a controller 119. As illustrated in FIG. 1, the controller is housed within the bed. In various embodiments the controller can be housed in either the mattress, base or be located externally outside of the bed. In some embodiments the controller comprises one or more processors. In some embodiments the controller is comprised of more than one processor, and the controller may be partitioned and housed in at least two separate physical enclosures, each with at least one processor. In some embodiments the controller is coupled to a network by way of wired or wireless communication circuitry, which may include for example antenna 114. In such embodiments the controller may be coupled (for example by a network 130 which may include the Internet) to a remote server 131, which in some embodiments may perform various of the functions ascribed to the controller herein. The controller is configured to command operations of the heating/cooling component, by program instructions executed by the controller in some embodiments, so as to result in desired sleep surface temperatures. In doing so, the controller receives signals from temperature sensors 115a,b. The temperature sensors are positioned in or adjacent the sleep surface, and provide an indication of a temperature of the sleep surface. In some embodiments, the temperature sensors are worn by the sleeper, provide an indication of a temperature of the sleeper's body or portion of body where the sensor is worn, and can be wired or wirelessly connected to the controller. In some embodiments, a first temperature sensor 115a is positioned to determine temperature of the sleep surface in an area over which a user's legs (or feet in some embodiments) may be expected to be placed, and a second temperature sensor 115b is positioned to determine temperature of the sleep surface in an area over which the user's torso is expected to be placed. In addition, some embodiments include an optional temperature sensor 112 for sensing ambient room temperature about the about the bed. In some embodiments desired sleep surface temperatures may be dependent, at least in part, on ambient room temperature. The embodiment of FIG. 1 shows the temperature sensor 112 on what may be considered a side of the foot of the bed, although in various embodiments the temperature sensor 112 may be located elsewhere.

In many embodiments the controller may also maintain a record of time-of day or time-of-year, and the controller may be configured to command adjustment of temperature based on time-of-day or time-of-year. For example, in some embodiments the controller may be configured to command temperature of the sleep surface to a first temperature at a first particular time of day, for example a time somewhat before or at a time of day the user is expected to lie on the sleep surface for the purpose of sleeping. The first temperature may be considered a warm temperature in some embodiments. In some embodiments the first temperature may be a temperature based, at least in part, on the ambient room temperature. In some embodiments the controller may be configured to command temperature of the sleep surface to a second temperature at a second particular time of day, for example a time at which the user is expected to fall asleep, or slightly afterwards (for example 15 minutes afterwards), on the sleep surface. The second temperature may be considered a cool temperature in some embodiments. In some embodiments the second temperature also may be a temperature based, at least in part, on the ambient room temperature. In embodiments in which the controller also commands temperature of the sleep surface to the first temperature, which is not the case in all embodiments, the second temperature is lower than the first temperature. In some embodiments the controller is also configured to cease commanding temperature of the sleep surface to the second temperature at a third particular time of day, for example a time at which the user is expected to have completed two complete sleep cycles, or slightly afterwards. In some embodiments the controller may be configured to command the temperature of the sleep surface to a third temperature (which may be the same as the first temperature) at a third particular time of day, for example a time at which precedes the time the user is expected to awaken, for example a time 30 or 45 minutes prior to the time the user is expected to awaken.

For example, in some embodiments the controller may be configured to command temperature of the sleep surface to a first temperature at a first particular time of year, for example a time during winter when the daylight period is shorter and the sleeper may typically go to bed at an earlier time than summer when the sleeper may typically go to bed a later time. In some embodiments the first temperature may also vary depending on the time-of-year in some embodiments, for example during the winter the first temperature may be set to a warmer temperature and during the summer the first temperature may be set to a cooler temperature. In some embodiments, the first temperature may be set as a targeted temperature differential to ambient temperature, for example during the winter the first temperature may be set to a temperature a fixed amount higher than ambient temperature and during the summer the first temperature may be set to a fixed amount lower than ambient temperature. In some embodiments the controller may be configured to command temperature of the sleep surface to a second temperature at a second particular time of day, for example a time at which the user is expected to fall asleep, or slightly afterwards (for example 15 minutes afterwards), on the sleep surface. This second temperature may also depend on the time-of-year in some embodiments, for example during the winter the second temperature may be set to a warmer temperature and during the summer the second temperature may be set to a cooler temperature. In some embodiments the second temperature also may be a temperature based, at least in part, on the ambient room temperature. In some embodiments, the second temperature may be set as a targeted temperature differential to ambient temperature, for example during the winter the second temperature may be set to a temperature a fixed amount higher than ambient temperature and during the summer the second temperature may be set to a fixed amount lower than ambient temperature. In embodiments in which the controller also commands temperature of the sleep surface to the first temperature, which is not the case in all embodiments, the second temperature is lower than the first temperature. In some embodiments the controller may be configured to command the temperature of the sleep surface to a third temperature (which may be the same as the first temperature) at a third particular time of day, for example a time at which precedes the time the user is expected to awaken, for example a time 30 or 45 minutes prior to the time the user is expected to awaken. Like the first and second temperatures described in this paragraph, this third temperature may also depend on the time-of-year in some embodiments.

In some embodiments the controller may include a wireless communication interface. In such embodiments the user may provide information to the controller regarding expected time of being on the sleep surface for sleep, and in some embodiments, expected awakening time, through use of a wireless communication capable device. The wireless communication capable device may be, for example, a smartphone or other device.

In some embodiments the controller may also receive information from a pressure sensor 117 and/or biometric sensors 118. The pressure sensor may be located under the sleep surface, and provide an indication of pressure on the sleep surface. Alternatively, the pressure sensor may be located in the controller and connected via air tubes to air chambers underneath the sleep surface to measure the pressure in the air chambers. The biometric sensors may be located in or under the sleep surface, and may provide an indication of heart rate, breathing information, or other biometric information regarding the user on the sleep surface. In some embodiments the biometric sensors may be in an article worn by the user, for example a shirt or wristband, with the biometric sensors communicating with the controller, either wired or wirelessly. In some embodiments the biometric sensors are as discussed or part of an item as discussed in J. Kelly et al., Recent Developments in Home Sleep-Monitoring Devices, ISRN Neurology, vol. 2012, article ID 768794, the disclosure of which is incorporated herein for all purposes.

In some embodiments the controller uses the information from the pressure sensor to determine when the user lies on the sleep surface and exits the sleep surface. In some such embodiments the controller may determine a time of day the user lies on the sleep surface to go to sleep based on the information from the pressure sensor, and extrapolate from this determination a time of day/night the user falls asleep on the sleep surface, for example by assuming a set predefined period between the time the user lies on the sleep surface and the time the user falls asleep on the sleep surface. In some embodiments the controller may determine that the user has fallen asleep by monitoring both when the pressure sensor indicates the user lies on the sleep surface, and by monitoring when the pressure sensor indicates a relatively constant pressure, indicating a lack of movement on the part of the user, or alternatively monitoring the output of a motion sensor located in the bed. Similarly, the controller may, in reverse, determine that a user has awoken and/or left the bed based on the information from the pressure sensor.

In some embodiments the controller uses the information from the biometric sensors to determine a sleep stage of the user. In some embodiments the sleep stage of the user may be considered to four stages of non-REM sleep—stages N1, N2, N3, N4, with stages N3 and N4 considered deep non-REM sleep or "slow-wave" sleep, —and one stage of REM sleep. In such embodiments, a user may be considered to typically undergo four full sleep cycles in a single night's sleep, with the first two sleep cycles being non-REM dominant and the last two sleep cycles being REM dominant. The first two sleep cycles typically include stage N1, N2, N3, N4 and REM, and the last two sleep cycles typically only include stages N1, N2, and REM. The sleep stage of the user may be determined using information from the biometric sensors, for example in manner utilizing or mimicking polysomnography techniques. In some embodiments the controller determines the sleep stage of the user by using one or more of its processors to compute the sleep stage based on information from the biometric sensors. In some embodiments, the controller communicates with a remote compute server over its communication interface, and the remote compute server computes the sleep stage based on biometric sensor information sent over the communication interface and may send sleep stage information back to the controller.

In embodiments in which the controller uses the information from the biometric sensors to determine a sleep stage of the user, the controller may command temperature of the sleep surface based on when the user falls asleep, completes two sleep cycles, etc., instead of basing those commands on times of day when the user is expected to fall asleep, complete two sleep cycles, etc.

In some embodiments the controller adaptively modifies the times and/or temperatures which the controller may command for the sleep surface, and in some embodiments does so in an iterative manner. In various embodiments an iterative process for determining improved outcomes (e.g. greater slow wave sleep duration, awakening in the lightest sleep cycles, or greater amount of uninterrupted total sleep) may be applied to one, some, or each of the timing parameters (t1, t2, t3, t4, t5) and temperature parameters (T1, T2, T3, T4, TA1, TA2, TA3, TA4) shown in FIG. 9. For example, in some embodiments the controller may command the sleep surface to a temperature somewhat below (or above) the second temperature, T2, for example 3 or 5 degrees F. below the second temperature, during the first two sleep cycles, and monitor duration of deep non-REM sleep of the user during that period, t3. If the duration of deep non-REM sleep with the cooler (or warmer) temperature is greater than duration of deep non-REM sleep than with the sleep surface set to the second temperature, T2, then a value for the second temperature is replaced with a value for the cooler (or warmer) temperature. In this regard, considering that determination of sleep stages may not always be accurate, in some embodiments multiple night's sleep may be monitored with the sleep surface set to various temperatures prior to updating or replacing the value used for the second temperature. In addition, in some embodiments at times the controller may not command any temperature for the sleep surface during some nights, with the controller simply monitoring duration of deep non-REM sleep during the first two sleep cycles in order to determine a baseline for later comparisons at differing temperature values. In some embodiments, this computation to determine replacement values for the second temperature is performed on a processor in the controller, and in other embodiments, this computation is performed on a remote server connected to the controller over a network.

Similarly, in some embodiments the controller may determine a sleep stage of the user at time of awakening, and modify, iteratively in some embodiments, a heating and/or temperature profile over time for period prior to an expected wake time of the user depending on the sleep stage at the time of awakening. For example, if a user awakens from a sleep stage other than a lightest non-REM sleep stage, N1, the controller may increase a commanded temperature, T3, and/or duration, t4, for heating for the sleep surface in the future. If the increased temperature and/or duration values results in the user awakening at a lighter non-REM sleep stage, these new values can be used to replace the original values of T3 and/or t4. In some embodiments, multiple night's sleep may be monitored with the sleep surface set to various value prior to updating or replacing the value currently used. In some embodiments, this computation to determine these replacement values is performed on a processor in the controller, and in other embodiments, this computation is performed on a remote server coupled to the controller over a network. In some embodiments the controller may be considered as using temperature to awaken the user, with the controller for example commanding heating to raise the user's core temperature to naturally lift the user out of deep sleep and into lighter stages of sleep. Raising the user's core temperature may help in awakening the user a person's natural circadian rhythm may be tied to body core temperature.

Figure 2:
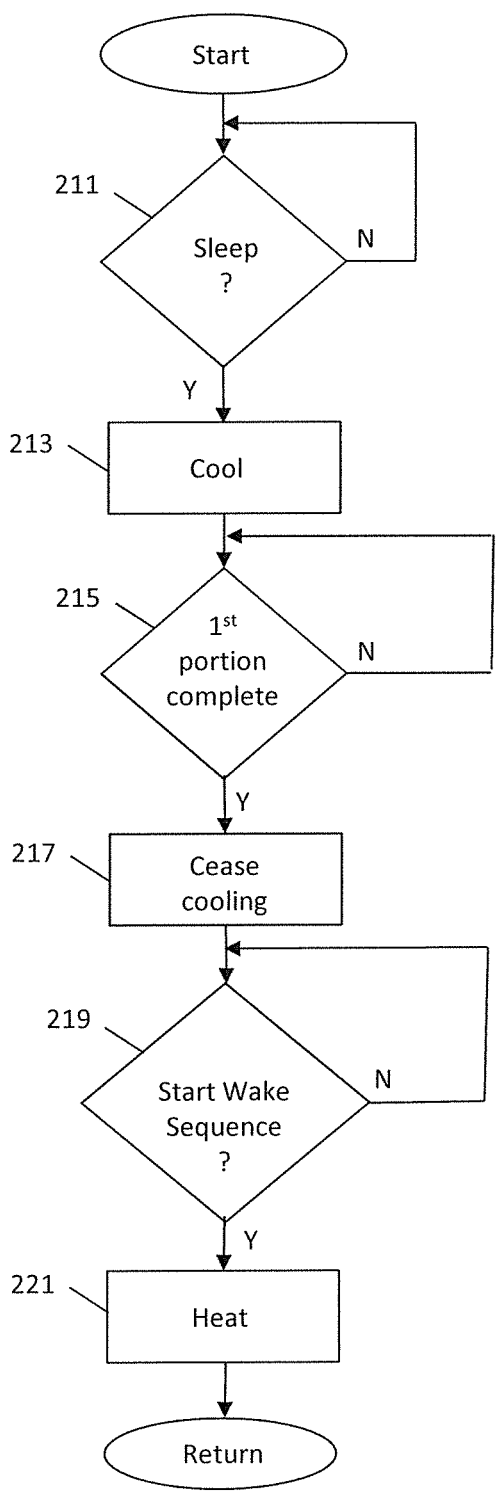
FIG. 2 is a flow diagram of a process for adjusting temperature of a sleep surface in accordance with aspects of the invention.

FIG. 2 is a flow diagram of a process for adjusting temperature of a sleep surface in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor, and in other embodiments, this computation is performed on a remote server coupled to the controller over a network. In some embodiments the processor receives information indicative of one or more temperatures of, or proximate, a sleep surface of a bed. In some embodiments the processor receives information from a pressure sensor indicating pressure on at least a portion of the sleep surface, and in some embodiments the processor receives information from biometric sensors of the bed, or associated with a user of the bed.

In block 211 the process determines whether a user is asleep on a sleep surface of a bed. In some embodiments the process determines that the user is asleep on the sleep surface based on an indication of a time of day, with for example the processor maintaining an indication of time of day. In some embodiments the process determines that the user is asleep on the sleep surface based on an indication from a pressure sensor that the user is on the sleep surface, in some embodiments relatively motionless, and in some embodiments also that the user has been on the sleep surface for a predetermined duration. In some embodiments the process determines that the user is asleep on the sleep surface based on information from biometric sensors.

If the user is not determined to be asleep on the sleep surface, the process repeats the operations of block 211. Otherwise the process continues to block 213.

In block 213 the process commands or sets a temperature of the sleep surface to a temperature. In some embodiments the temperature is the second temperature discussed elsewhere herein. In some embodiments the temperature is a temperature cooler than a temperature of the sleep surface at a time prior, immediately prior in some embodiments, to the user being determined to be asleep. In some embodiments the process commands or sets the temperature of the sleep surface by issuing commands or causing operation of a heating and/or cooling component of the bed. In some embodiments the process commands or sets the temperature of the sleep surface based on indications of sleep surface temperature provided by temperature sensors providing such indications. Accordingly, the process may command or set the temperature of the sleep surface to a temperature cooler than an indication of sleep surface temperature provided by temperature sensors at a time prior to, immediately prior to in some embodiments, to the user being determined to be asleep. In some embodiments the temperature may be up to five degrees Fahrenheit cooler than the temperature of the sleep surface indicated by the temperature sensors at the time prior to, immediately prior to in some embodiments, the user being determined to be asleep. In some embodiments the time prior to the user being determined to be asleep is a time after the user has entered the bed and at least one temperature sensor, or a plurality of temperature sensors in some embodiments, indicates that the sleep surface has reached a stable temperature (for example in view of heating of the sleep surface due to the user's body heat).

In block 215 the process determines if a first portion of a night's sleep has been completed. In some embodiments the first portion of the night's sleep is two complete sleep cycles. In some embodiments the two complete sleep cycles are a first two sleep cycles of the night's sleep. In some embodiments the first portion of the night's sleep is a non-REM dominant portion of the night's sleep. In some embodiments the process determines if the first portion of the night's sleep has been completed based on time of day. In some embodiments the process determines if the first portion of the night's sleep has been completed based on information from a pressure sensor and any indications of time of day. In some embodiments the process determines if the first portion of the night's sleep has been completed based on a predetermined amount of time has transpired after the user falls asleep. In some embodiments the process, instead or in addition, determines if the first portion of the night's sleep has been completed-based on information from biometric sensors.

If the process determines that the first portion of the night's sleep has been completed, the process continues to block 217. In block 217 the process ceases commanding or setting a temperature of the sleep surface to the temperature. In some embodiments, turning off temperature control after the first portion of sleep allows the body's natural body temperature to warm the sleep surface and allow for relatively warmer temperature during the REM-dominated latter two sleep cycles.

In block 219 the process determines if a wake-up sequence should begin. In some embodiments the process determines a wake-up sequence should begin at a time of day that is a predetermined time before an expected waking time of the user. In some embodiments the expected waking time is determined based on prior awakening times of the user. In some embodiments the prior awakening times of the user is based on information from the pressure or biometric sensors, for example when the pressure sensor has indicated motion indicative of movement of the user. In some embodiments the expected waking time is determined as a time of day indicated by the user as a desired waking time. In some embodiments the predetermined time before the expected waking time of the user is between 5 and 90 minutes, in some embodiments is between 10 and 60 minutes, and in some embodiments is between 15 and 45 minutes.

If the process determines that the wake-up sequence should begin, the process proceeds to block 221. In block 221 the process sets or commands temperature of the sleep surface to another temperature. In some embodiments the other temperature is the third temperature discussed herein. In some embodiments the process may also activate one or more lighting devices, for example lighting devices coupled to the controller over a wireless connection. In some embodiments the process may also activate one or more diffusers, for example diffusers coupled to the controller over a wireless connection. In block 222, the process then determines whether the user is awake and has left the bed. In some embodiments, if the pressure sensor or biometric sensors indicates the user has left the sleep surface, the process ceases setting or commanding the temperature of the sleep surface to the other temperature or the process turns off the temperature control system.

In some embodiments the process also activates an alarm at the time awakening is desired or expected. Activating the alarm may help waken the user in case the temperature system has not fully wakened the user by their desired wake time. In some embodiments the alarm is an audio alarm. In some embodiments the alarm is a motion alarm, for example motion provided by inflating or deflating an air chamber in the bed or an actuator device. In some embodiments the alarm is a light alarm, in which one or more lighting devices that are connected to the controller over a wireless connection are activated. In some embodiments the alarm is a scent alarm, for example provided by a scent diffuser. In some embodiments the alarm includes a combination of audio, motion, or light, together with the temperature control system.

The process thereafter returns.

Figure 3:
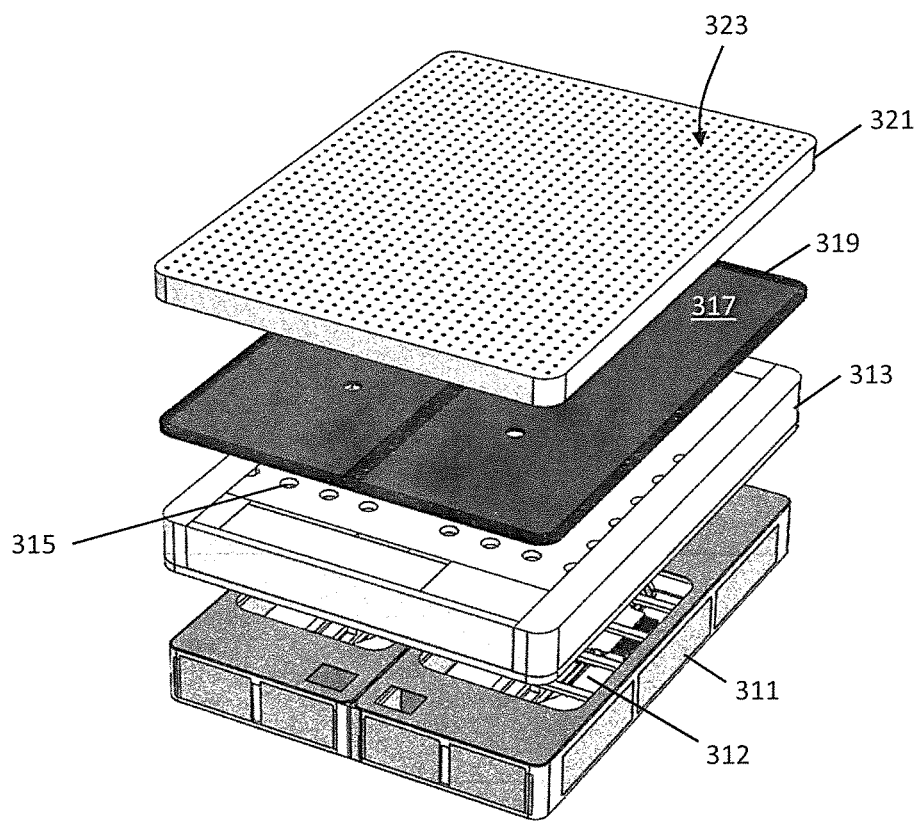
FIG. 3 is a diagrammatic expanded perspective view of a bed in accordance with aspects of the invention.

FIG. 3 is a diagrammatic exploded perspective view of a bed in accordance with aspects of the invention. The bed of FIG. 3 may be used as the bed of FIG. 1, in some embodiments. The bed of FIG. 3 may also be used in the process of FIG. 2, in some embodiments.

The bed of FIG. 3 includes a substantially rectangular parallelepiped base 311. The base includes one or more apertures 312 in its upper surface, providing access to a generally open interior of the base. The interior of the base may include, for example, a heating/cooling component, and in some embodiments a controller for controlling the heating/cooling component and other controllable aspects of the bed (although in various embodiments the controller may be elsewhere located in, on, or about the structure of the bed). The apertures in the upper surface of the bed may provide for airflow from the heating/cooling component towards a sleep surface 323 of the bed. In many embodiments legs extend under corners or other portions of the base, for example to allow for the base to be raised off of the floor when in use. In such embodiments the base may also include apertures in a lower surface of the base, for example to provide for further airflow. In some embodiments, and as illustrated in FIG. 3, the base may in fact be two separate bases, positioned to about one another in a side-by-side configuration.

A mattress of the bed is atop the base. The mattress is comprised of a core 313, with a reticulated foam layer 317 (bounded by a border 319) above the core and a foam pad 321 above the reticulated foam. The core, like the base, is of a generally rectangular parallelepiped form, with generally the same dimensions as the base. The core includes apertures extending through the core, from an upper surface of the core to a lower surface of the core. The apertures allow for airflow from the base to the reticulated foam. The reticulated foam diffuses airflow from the core, such that air may diffusely reach the foam pad. Other embodiments may use other materials, such as other types of open structured fibers, that perform similar function of diffusing airflow.

The foam pad, in the embodiment of FIG. 3, also includes apertures through the pad, from an upper surface of the foam pad to a lower surface of the foam pad. The upper surface of the foam pad provides a sleep surface of the bed.

In operation, the heating/cooling component, under command of the controller, causes air of a desired temperature to exit the base and flow, through the core, reticulated foam, and pad, to the sleep surface.

Figure 4:
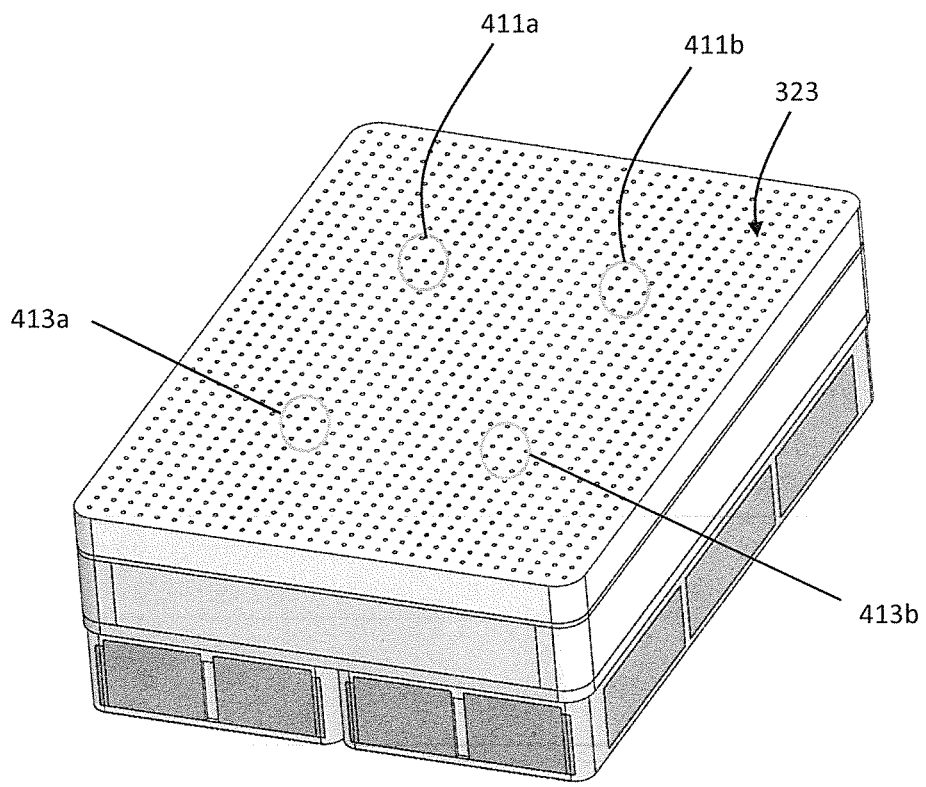
FIG. 4 is a perspective view of the bed of FIG. 3, illustrating temperature sensor positioning in accordance with aspects of the invention.

FIG. 4 is a perspective view of the bed of FIG. 3, illustrating temperature sensor positioning in accordance with aspects of the invention. The bed of FIG. 4 includes four temperature sensors, two each for each of two users who may simultaneously use the bed for sleeping. The temperature sensors are positioned in the foam pad, just under the sleep surface 323 of the bed. In the bed of FIG. 4, temperature sensors 411a,b are positioned so as to be effectively under torsos of a first user and a second user, respectively, of the bed. Temperature sensors 413a,b are positioned so as to be effectively under legs of a first user and a second user, respectively, of the bed. In operation, the controller may utilize information from the temperature sensors in commanding operation of the heating/cooling component. In addition, in some embodiments, a heating/cooling component is provided for each of the two users (or sides) of the bed, allowing for different heating and/or cooling of the sleep surface of the bed about the different users. Other embodiments may further partition each user side into more temperature zones, such as an upper and lower zone to allow for different temperatures for the lower and upper body of each user.

Figure 5:
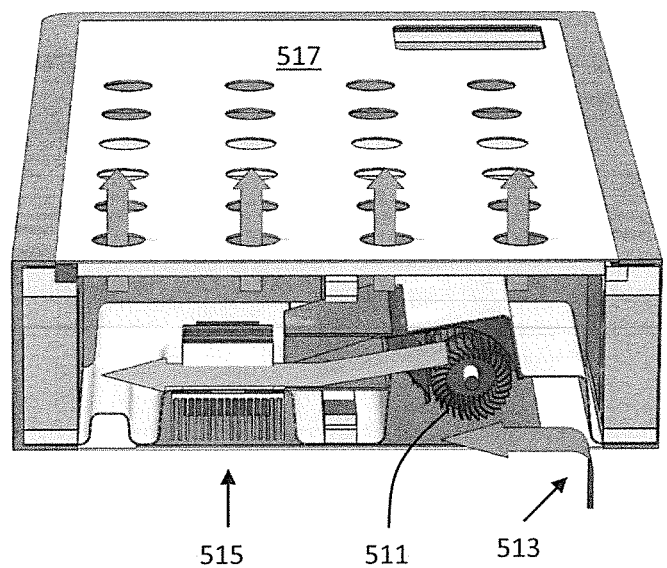
FIG. 5 illustrates a heating/cooling component in a base of a bed, in accordance with aspects of the invention.

FIG. 5 illustrates a heating/cooling component in a base of a bed, in accordance with aspects of the invention. The heating/cooling component and the base may be used, for example in the bed of FIG. 1 or FIGS. 3 and 4.

An interior of the base houses a fan 511. The fan draws air from an opening 513 in a bottom surface of the base, and directs air towards a thermoelectric device 515. In some embodiments the thermoelectric device is a Peltier device, and provides both heating and cooling, as commanded, for the air. The heated or cooled air exits an upper surface of the base, through apertures in the upper surface.

Figure 6:
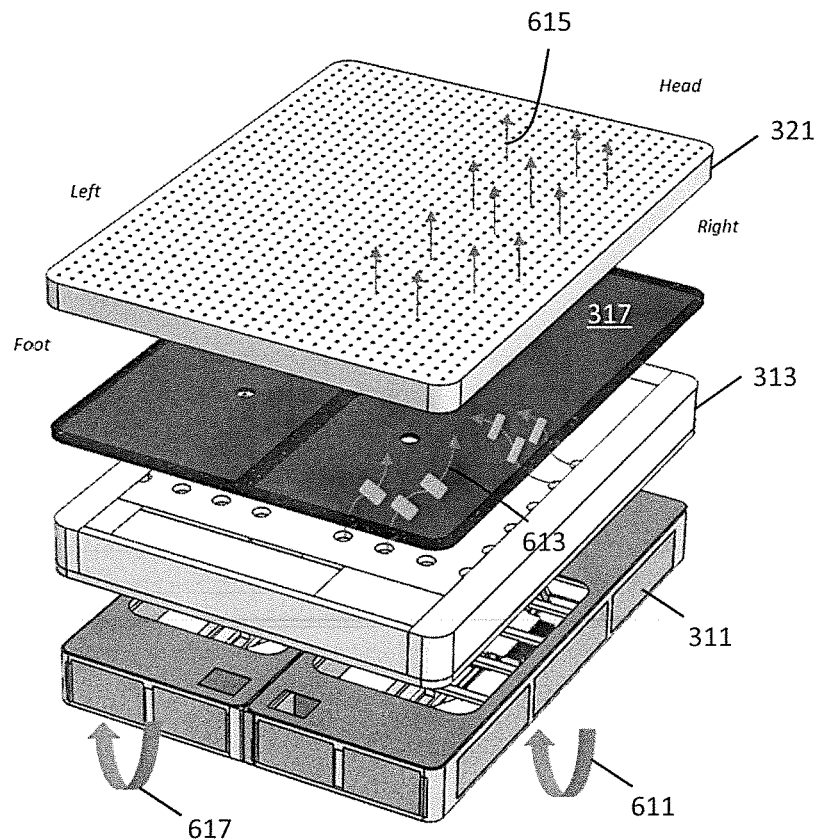
FIG. 6 illustrates airflow for the bed of FIG. 3 with a temperature control unit of FIG. 5, in accordance with aspects of the invention.

FIG. 6 illustrates airflow for the bed of FIG. 3 with a temperature control unit of FIG. 5, in accordance with aspects of the invention.

In FIG. 6, intake air 611 enters the base through one or more apertures in a lower surface of the base, in which the air is conditioned by heating or cooling. The heated or cooled air 613 flows through apertures in the core 313, and diffused in a layer of reticulated foam 317. The diffused heated or cooled air 615 then flow through apertures in the foam pad 321. In addition, in some embodiments some exhaust air 617, flows out of the base, through further apertures in the lower surface of the base. In other embodiments, the air may be directed to the sleep surface through tubes, or channels, or other structures for directing air.

Figure 7:
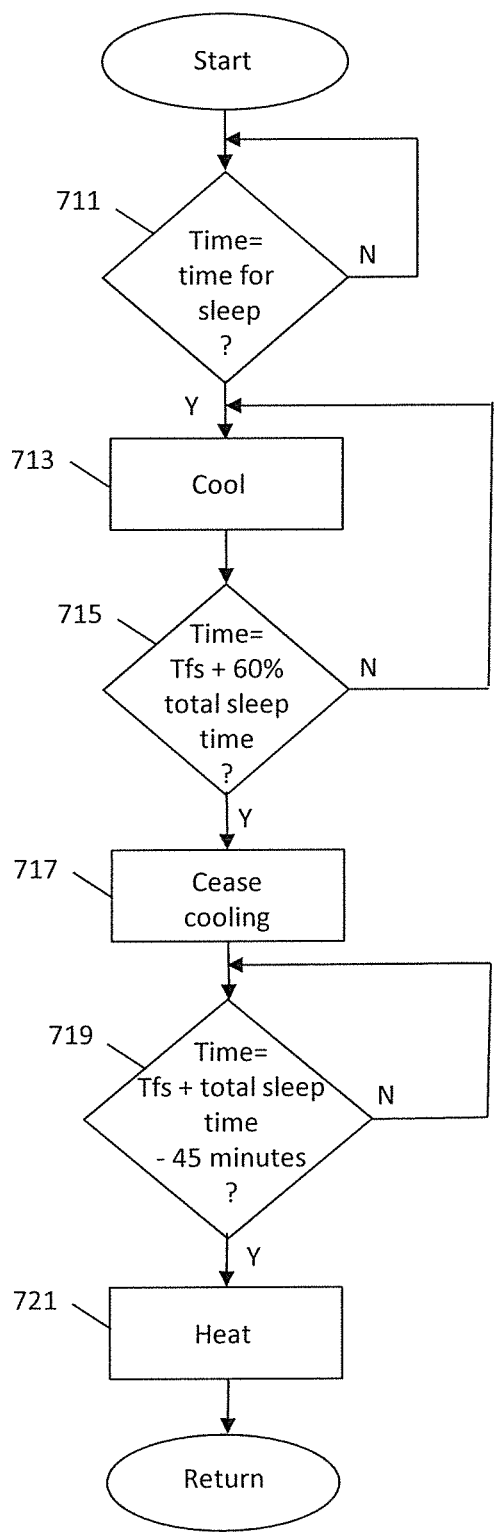
FIG. 7 is a further flow diagram of a process for adjusting temperature of a sleep surface based on time in accordance with aspects of the invention.

FIG. 7 is a further flow diagram of a process for adjusting temperature of a sleep surface based on time in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor, and in other embodiments, this computation is performed on a remote server coupled to the controller over a network. In some embodiments the processor receives information indicative of one or more temperatures of, or proximate, a sleep surface of a bed. In some embodiments the processor receives information from a pressure sensor indicating pressure on at least a portion of the sleep surface. In some embodiments the process of FIG. 7 performs the process of FIG. 2, utilizing time for determination of heating/cooling operations.

In block 711 the process determines whether a time of day indicates that it is time for a user to sleep on a sleep surface of a bed. In some embodiments the process determines that it is time for the user to sleep based on an indication of a time of day, with for example the processor maintaining an indication of time of day. In some embodiments the process determines that the time for the user to sleep user based on an indication from a pressure sensor or biometric sensor that the user is on the sleep surface, in some embodiments relatively Motionless, and in some embodiments also that the user has been on the sleep surface for a predetermined duration.

If the process determines that it is not yet time for sleep, the process repeats the operations of block 711. Otherwise the process continues to block 713.

In block 713 the process commands or sets a temperature of the sleep surface to a temperature. In some embodiments the temperature is the second temperature discussed elsewhere herein. In some embodiments the temperature is a temperature cooler than a temperature of the sleep surface at a time prior, immediately prior in some embodiments, to the time for sleep. In some embodiments the process commands or sets the temperature of the sleep surface by issuing commands or causing operation of a heating and/or cooling component of the bed. In some embodiments the process commands or sets the temperature of the sleep surface based on indications of sleep surface temperature provided by temperature sensors providing such indications.

In block 715 the process determines if the time indicates that the user has completed a first portion of a night's sleep time. In some embodiments, the first portion of the night's sleep time is a portion of the sleep time in which the user completes two full sleep cycles. In some embodiments the user is expected to have completed two full sleep cycles after completing a first sixty percent of a total night's sleep time. Accordingly, in some embodiments the process determines if a current time is equal to the time at time of sleep plus a percentage of the total sleep time (e.g. 60%).

If the process determines that the first portion of the night's sleep has been completed, the process continues to block 717. In block 717 the process ceases commanding or setting a temperature of the sleep surface to the temperature.

In block 719 the process determines if a wake up sequence should begin. In some embodiments the process determines a wake up sequence should begin if a time of day is a predetermined time before an expected waking time of the user. In some embodiments the expected waking time is determined as a time of day indicated by the user as a desired waking time. In some embodiments the predetermined time before the expected waking time of the user is a fixed time, (e.g. 45 minutes).

If the process determines that the wake up sequence should begin, the process proceeds to block 721. In block 721 the process sets or commands temperature of the sleep surface to another temperature. In some embodiments the other temperature is the third temperature discussed herein. In some embodiments the process ceases setting or commanding the temperature of the sleep surface to the other temperature if the pressure sensor indicates the user has left the sleep surface.

In some embodiments the process also activates an alarm at the time awakening is desired or expected. In some embodiments the alarm is an audio alarm. In some embodiments the alarm is a motion alarm, for example motion provided by inflating or deflating an air chamber in the bed or an actuator device. In some embodiments the alarm is a light alarm, in which one or more lighting devices that are connected to the controller over a wireless connection are activated. In some embodiments the alarm includes a combination of audio, motion, or light, together with the temperature control system.

The process thereafter returns.

Figure 8:
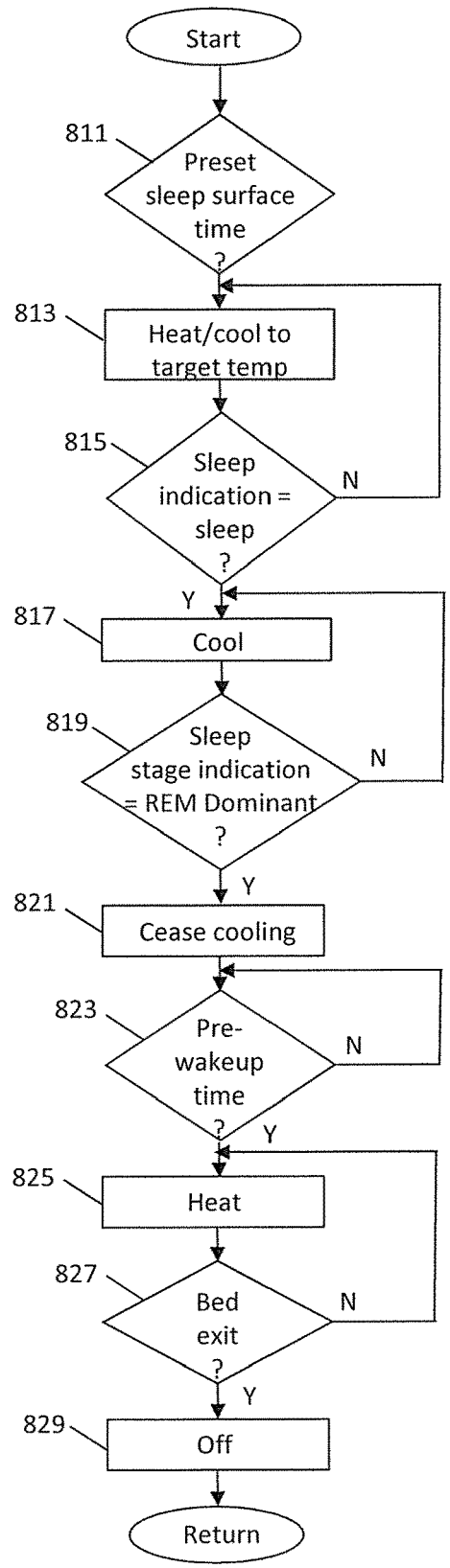
FIG. 8 is a further flow diagram of a process for adjusting temperature of a sleep surface based on sleep status and time in accordance with aspects of the invention.

FIG. 8 is a further flow diagram of a process for adjusting temperature of a sleep surface based on sleep status and time in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor and in other embodiments, this computation is performed on a remote server connected to the controller over a network. In some embodiments the processor receives information indicative of one or more temperatures of, or proximate, a sleep surface of a bed. In some embodiments the processor receives information from a pressure sensor indicating pressure on at least a portion of the sleep surface, and in some embodiments the processor receives information from biometric sensors of the bed, or associated with a user of the bed.

In block 811 the process determines if the time of day indicates a preset time prior to presence of a user on a sleep surface of the bed for purposes of sleep. In some embodiments the preset time is a time preset by the user, for example using a smartphone or handheld remote device in communication with a controller of the bed. In some embodiments the controller determines the preset time based on prior usage of the bed, for example during previous days, and the time it takes for the temperature control system to reach a target temperature. In some such embodiments the controller may determine, for example using a pressure sensor, when a user entered the bed on previous days, and was relatively still. In some such embodiments the controller may track such usage on a day of the week basis, allowing for the preset time to be different on different days of the week.

If the process determines that it is the preset time, the process continues to block 813.

In block 813 the process heats or cools the bed, heat in most embodiments, to a first temperature. In some embodiments the process determines if the sleep surface has reached the first temperature prior to the user entering the bed. In some embodiments the user may be considered to have entered the bed at a predetermined time-of-day. In some embodiments the user may be considered to have entered the bed based on information from pressure sensors of the bed, or other sensors. If the sleep surface did not reach the first temperature prior to the user entering the bed, in some embodiments the process changes the preset time to an earlier time. Conversely, the process may also determine if the sleep surface reached the first temperature at a time earlier than the user entered the bed. If the difference in time between the earlier time and the time the user entered the bed is greater than a predetermined amount of time, the process may change the preset time to a later time.

In block 815 the process determines whether a user is asleep on a sleep surface of a bed. In some embodiments the process determines that the user is asleep on the sleep surface based on information from biometric sensors.

If the user is not determined to be asleep on the sleep surface, the process repeats the operations of block 815. Otherwise the process continues to block 817.

In block 817 the process commands or sets a temperature of the sleep surface to a second temperature. In some embodiments the temperature is the second temperature discussed elsewhere herein. In some embodiments the second temperature is a temperature cooler than the first temperature. In some embodiments the process commands or sets the temperature of the sleep surface by issuing commands or causing operation of a heating and/or cooling component of the bed. In some embodiments the process commands or sets the temperature of the sleep surface based on indications of sleep surface temperature provided by temperature sensors providing such indications.

In block 819 the process determines if a first portion of a night's sleep has been completed. In some embodiments the first portion of the night's sleep is two complete sleep cycles. In some embodiments the two complete sleep cycles are a first two sleep cycles of the night's sleep. In some embodiments the first portion of the night's sleep is a non-REM dominant portion of the night's sleep. In some embodiments the process determines if the first portion of the night's sleep has been completed based on information from biometric sensors. In some embodiments the process determines that the first portion of the night's sleep has been completed if the information from the biometric sensors indicates that the user's sleep stage is an REM dominant sleep stage.

If the process determines that the first portion of the night's sleep has been completed, the process continues to block 821. In block 821 the process ceases commanding or setting a temperature of the sleep surface to the second temperature.

In block 821 the process determines if a wake-up sequence should begin. In some embodiments the process determines a wake-up sequence should begin if a time of day is a predetermined time before an expected waking time of the user. In some embodiments the expected waking time is determined based on prior awakening times of the user. In some embodiments the prior awakening times of the user is based on information from the pressure sensor, for example when the pressure sensor has indicated motion indicative of movement of the user. In some embodiments the expected waking time is determined as a time of day indicated by the user as a desired waking time. In some embodiments the predetermined time before the expected waking time of the user is forty-five minutes.

If the process determines that the wake-up sequence should begin, the process proceeds to block 825. In block 825 the process sets or commands temperature of the sleep surface to another temperature. In some embodiments the other temperature is the third temperature discussed herein. In some embodiments the process ceases setting or commanding the temperature of the sleep surface to the other temperature if the pressure sensor indicates the user has left the sleep surface.

In some embodiments the process also activates an alarm at the time awakening is desired or expected. In some embodiments the alarm is an audio alarm. In some embodiments the alarm is a motion alarm, for example motion provided by an inflation or deflation of an air bladder in the bed. In some embodiments the alarm is a light alarm, in which one or more lighting devices are activated.

In block 827 the process determines if the user has left the bed. If not, the process continues with operations of block 825. Otherwise the process ceases commanding or setting the temperature of the sleep surface in block 829, and the process thereafter returns.

Figure 9:
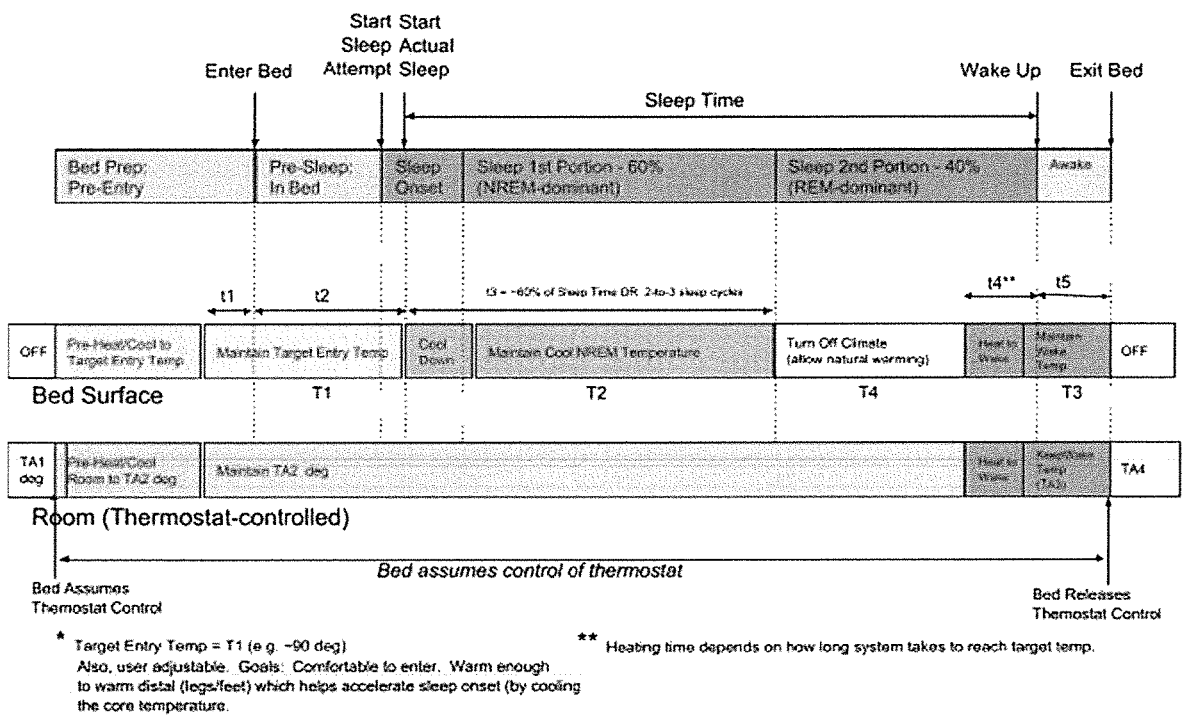
FIG. 9 is a timing diagram of sleep status and temperature operations in accordance with aspects of the invention.

FIG. 9 is a timing diagram of sleep status and temperature operations in accordance with aspects of the invention. In some embodiments the temperature operations are commanded by a controller of the bed, or associated with the bed in some embodiments. In some embodiments the temperature operations are performed by the bed of FIG. 1 and, in some instances, a heating/cooling apparatus for a room in which the bed is located, or a dwelling or other housing in which the bed is located.

The timing diagram includes a first line indicating user status with respect to the bed, a second line indicating bed sleep surface temperature control, and a third line indicating ambient temperature of a room in which the bed is located.

At a first time, control of the bed sleep surface is off, and control of room temperature is performed independently of the bed controller, with control of room temperature performed by a thermostat, for example. At a second time, prior to a user entering the bed, the controller commands the temperature of the sleep surface to a target entry temperature, T1. The target entry temperature may be the first temperature discussed herein. In some embodiments the controller also commands a room/dwelling temperature controller (e.g. a thermostat) to command an ambient temperature of the room to a predetermined first room temperature, TA2, which may be 69 degrees Fahrenheit in some embodiments. The controller may command the room/dwelling temperature controller by way of wireless communication circuitry included with the controller or of the bed and coupled to the controller. In some embodiments the controller determines the second time based on a past history of times when the user had entered the bed, for example as indicated by a pressure sensor or other sensor of the bed. In some embodiments the controller determines the second time by subtracting a predetermined time, for example 30 or 45 minutes, from the expected entry time.

In the timing diagram of FIG. 9, the sleep surface reaches the target temperature, T1, at a duration, t1, before the expected entry time. In some embodiments the ambient temperature of the room also reaches the commanded temperature at a similar time.

The user enters the bed at a third time. In some embodiments the controller receives an indication that the user entered the bed from a sensor of the bed, for example a pressure sensor.

At a fourth time the user begins sleeping. In some embodiments the controller receives information from biometric sensors of the bed, from which the controller can determine that the user is sleeping, for example by determining that the sleeper has entered the N1 sleep stage. In some embodiments the controller determines that the user is sleeping based on an indication, for example from a pressure sensor or other sensor, of lack of movement by the user over a period of time.

In the timing diagram of FIG. 9, the controller commands the temperature of the sleep surface to a cool non-REM temperature, T2, for example the second temperature discussed herein, after the user has begun sleeping. The controller commands maintenance of the sleep surface at this temperature for non-REM dominant sleep period of the user, t3. In some embodiments the non-REM dominant sleep period, t3, is a predetermined percentage (e.g. 60%) of a total sleep period for the user. In some embodiments the non-REM dominant sleep period, t3, is the duration of the first two stages or some duration between the first two and three sleep stages. In some embodiments, after the user begins sleeping, the controller commands the room/dwelling temperature controller (e.g. a thermostat) to command an ambient temperature of the room to a predetermined second room temperature, TA2, which may be cooler than the first room temperature (e.g. 66 degrees Fahrenheit).

At the end of the non-REM dominant sleep period, the controller ceases commanding a target temperature for the sleep surface, until a predetermined time prior to expected user awakening.

At a duration prior to the user wake up time, t4, for example 45 minutes prior to the user awakening time, the controller commands the temperature of the sleep surface to a third temperature, T3, for example the third temperature discussed herein. Preferably, the temperature of the sleep surface reaches the third temperature prior to the user wake up time and the heating time may be set such that the sleep surface will reach the third temperature by that time (considering the delays between a time of commanding a temperature and the sleep surface reaching that temperature). In some embodiments the third temperature is 72 degrees Fahrenheit. In some embodiments the controller also commands the room/dwelling temperature controller to set a temperature of the room to a predetermined third room temperature, TA3, which also may be warmer than the second room temperature, TA2 (e.g. 72 degrees Fahrenheit).

Finally, the user exits the bed and upon detecting the user exit from the bed sensors, such as the pressure sensors, the controller turns off the heating/cooling component used for setting sleep surface temperature, and ceases control, if any, of or relating to the room/dwelling temperature controller.

Figure 10:
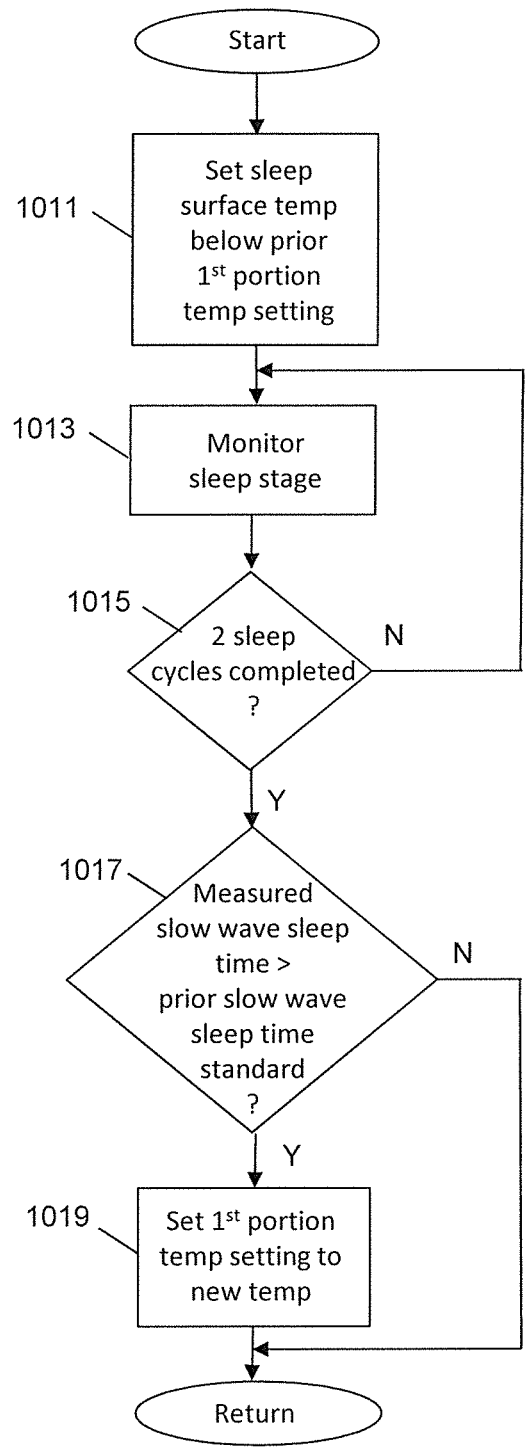
FIG. 10 is a flow diagram of a process for determining a temperature of a sleep surface during a portion of a sleep time in accordance with aspects of the invention.

FIG. 10 is a flow diagram of a process for determining a temperature of a sleep surface during a portion of a sleep time in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor and in other embodiments, this computation is performed on a remote server coupled to the controller over a network. In some embodiments the processor receives information indicative of one or more temperatures of, or proximate, a sleep surface of a bed. In some embodiments the processor receives information from a pressure sensor indicating pressure on at least a portion of the sleep surface, and in some embodiments the processor receives information from biometric sensors of the bed, or associated with a user of the bed.

In block 1011 the process commands temperature of the sleep surface to a temperature other than a temperature to which the process would otherwise command the sleep surface for a first portion of a user's night's sleep. In some embodiments the process would otherwise command the sleep surface to the second temperature, as discussed herein, for the first portion of the user's night's sleep, and in block 1011 the process instead commands the temperature of the sleep surface to some other temperature. In some embodiments the some other temperature is three to five degrees Fahrenheit cooler than the second temperature, or up to five degrees Fahrenheit cooler in some embodiments. In some embodiments the different temperature is provided to the bed, or the controller of the bed, by a remote server. In some embodiments the remote server determines the different temperature based on sleep information of other sleepers. In various embodiments the process performs operations of block 1011 upon the user falling asleep, or within half an hour of the user falling asleep, for example as indicated from information from sensors associated with the bed or user.

In block 1013 the process monitors sleep stages of the user. In some embodiments the process monitors sleep stages of the user using biometric sensors. In some embodiments the sleep stages of the user include a light sleep stage, for example sleep stages N1 and N2, deep sleep stages, for example stages N3 and N4, and a REM sleep stage. In some embodiments the deep sleep stages may be considered non-REM slow wave sleep.

In block 1015 the process determines if the user has completed two full sleep cycles. In some embodiments, the process determines if the user has completed at least two full sleep cycles but no longer than three sleep cycles. If not, the process continues monitoring sleep stages of the user in block 1013. Otherwise the process continues to block 1017.

In block 1017 the process determines if the user spent more time in non-REM slow wave sleep with the temperature commanded to the some other temperature than in the first two sleep cycles (or at least two sleep cycles but no longer than three sleep cycles, in some embodiments) of prior nights with the sleep surface commanded to the second temperature. In some embodiments the controller provides information regarding monitoring of sleep stages to a remote server, with the remote server making the determination. In some embodiments the process may perform the operations of blocks 1011-1015 multiple times across multiple nights, and use an average, or some other statistically calculated value, for determining whether the user experienced more non-REM slow wave sleep with the temperature commanded to the some other temperature than with the temperature commanded to the second temperature.

If the process determines that the user experienced more non-REM slow wave sleep with the temperature commanded to the some other temperature, in response the process changes the second temperature to be the some other temperature in block 1019. In some embodiments the process does so by setting a value in memory indicative of the temperature at which the sleep surface is to be commanded to be the some other temperature. In addition or instead, in some embodiments the process may vary a time during which the slow wave sleep time is monitored and compared. For example, the process may maintain the sleep surface at the second temperature for a longer period (for example into the third sleep cycle) or a shorter period, and monitor and compare slow wave sleep times. In such embodiments, the process may set a new (longer or shorter) period for use of the second temperature so as to increase slow wave sleep times.

The process thereafter returns.

Figure 11:
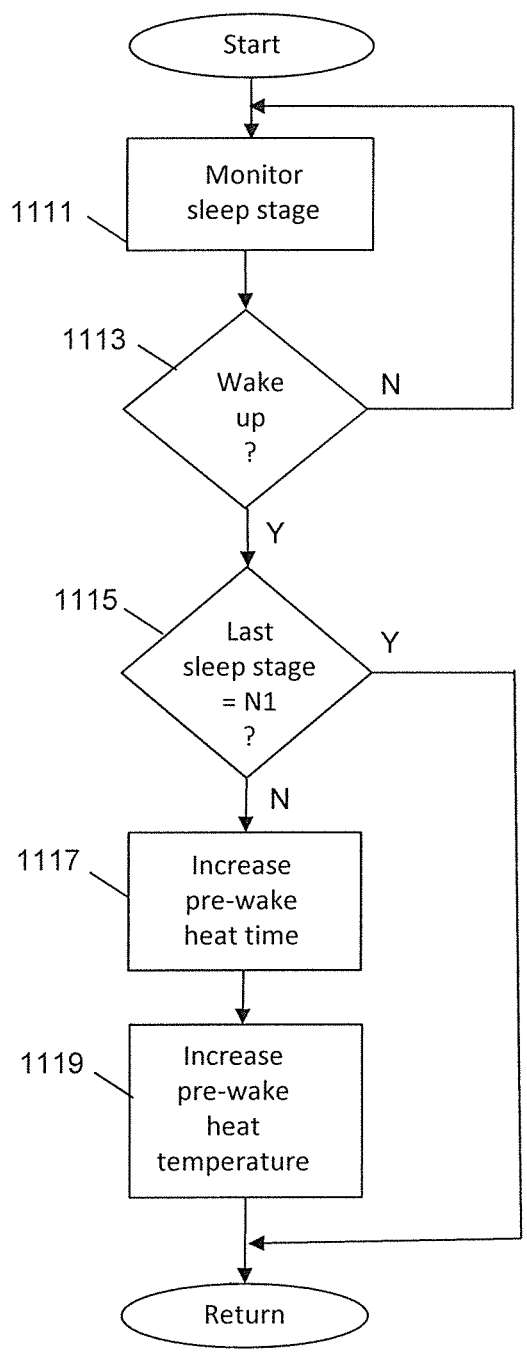
FIG. 11 is a flow diagram of a process for adjusting pre-wake temperature related operations for a sleep surface based on awakening conditions in accordance with aspects of the invention.

FIG. 11 is a flow diagram of a process for adjusting pre-wake temperature related operations for a sleep surface based on awakening conditions in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor and in other embodiments, this computation is performed on a remote server coupled to the controller over a network. In some embodiments the processor receives information indicative of one or more temperatures of, or proximate, a sleep surface of a bed. In some embodiments the processor receives information from a pressure sensor indicating pressure on at least a portion of the sleep surface, and in some embodiments the processor receives information from biometric sensors of the bed, or associated with a user of the bed.

In block 1111 the process monitors sleep stages of a user asleep on the sleep surface. In some embodiments the process monitors sleep stages using biometric sensors.

In block 1113 the process determines if the user has awoken. If not, the process continues monitoring sleep stages of the user in block 1111. If the user has awoken, the process continues to block 1115.

In block 1115, the process determines if the user was in a lightest sleep stage immediately prior to awakening. In some embodiments the lightest sleep stage is the N1 sleep stage. If the user was in the lightest sleep stage, the process returns. Otherwise the process continues to the operations of block 1117 and 1119.

In blocks 1117 the process increases a temperature to which the sleep surface is to be commanded as part of a wake-up sequence, a temperature that may be considered the third temperature as discussed elsewhere herein. In block 1119 the process increases an overall time for the wake-up sequence (and hence the amount of time the sleep surface is set to the third temperature). In some embodiments operations of only one of blocks 1117 and 1119 are performed.

The process thereafter returns.

Figure 12:
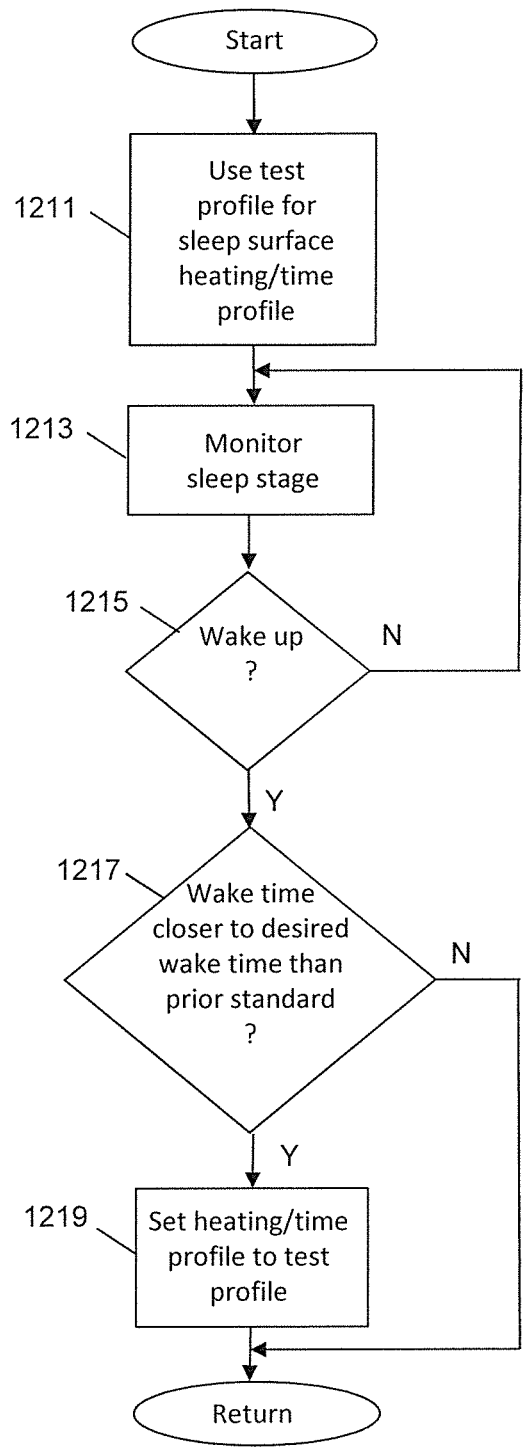
FIG. 12 is a further flow diagram of a process for adjusting pre-wake temperature related operations for a sleep surface based on awakening conditions in accordance with aspects of the invention.

FIG. 12 is a further flow diagram of a process for adjusting pre-wake temperature related operations for a sleep surface based on awakening conditions in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor and in other embodiments, this computation is performed on a remote server coupled to the controller over a network. In some embodiments the processor receives information indicative of one or more temperatures of, or proximate, a sleep surface of a bed. In some embodiments the processor receives information from a pressure sensor indicating pressure on at least a portion of the sleep surface, and in some embodiments the processor receives information from biometric sensors of the bed, or associated with a user of the bed.

In block 1211 the process uses a different time and temperature profile for commanding temperature of the sleep surface than a then current time and temperature profile for use as part of an awakening sequence for the user. In some embodiments the different time and temperature profile is provided to the bed by a remote server. In some embodiments the remote server determines the different time and temperature profile using information regarding other sleepers. In some embodiments the process commands temperature of the sleep surface to a temperature other than a temperature to which the process would otherwise command the sleep surface for the awakening sequence for the user. In some embodiments the process would otherwise command the sleep surface to the third temperature, as discussed herein, for the awakening sequence, and in block 1211 the process instead commands the temperature of the sleep surface to some other temperature. In some embodiments the some other temperature is three to five degrees Fahrenheit cooler, or warmer, than the third temperature. In some embodiments the process, instead or in addition, commands the sleep surface to the some other temperature at a different time than the process would otherwise do so as part of the awakening sequence. For example, the process may command the temperature of the sleep surface to the some other temperature a number of minutes, for example 5 minutes, sooner or later than the process would otherwise do as part of the awakening sequence.

In block 1213 the process monitors sleep stages of the user. In some embodiments the process monitors whether the user is asleep. In some embodiments the process monitors whether the user is asleep by determining if the user is in the bed, for example using a pressure sensor or motion sensor. In some embodiments the process determines if the user is asleep by determining if motion patterns, or lack thereof, of the user in the bed matches a pattern indicating sleep, with the motion patterns sensed by pressure and/or motion sensor. In some embodiments the process detects sleep stages of the user using biometric sensors. In some embodiments the sleep stages of the user include a light sleep stage, for example sleep stages N1 and N2, deep or slow wave sleep stages, for example stages N3 and N4, and a REM sleep stage, with a lack of a sleep stage indicating wakefulness on the part of the user.

In block 1215 the process determines if the user has woken up. If not, the process continues monitoring sleep stages of the user in block 1213. Otherwise the process continues to block 1217.

In block 1217 the process determines if the user woke up closer to a target wake up time with use of the different time and temperature profile than with the then standardly used time and temperature wake up sequence profile set for the user. In some embodiments the process only considers that the user woke up closer to the target wake up time if the user did not sleep past the target wake up time. In some embodiments the process may perform the operations of blocks 1211-1215 multiple times across multiple nights, and use an average, or some other statistically calculated value, for determining whether the user woke up closer to the target wake up time with use of the different time and temperature profile than with the then standardly used time and temperature wake up sequence profile set for the user.

If the process determines that the user woke up closer to the target wake up time, in response the process changes the then standardly used time and temperature wake up sequence profile to be the different time and temperature profile in block 1219. In some embodiments the process does so by setting a value or values in memory indicative of the time and temperature profile.

The process thereafter returns.

Figure 13:
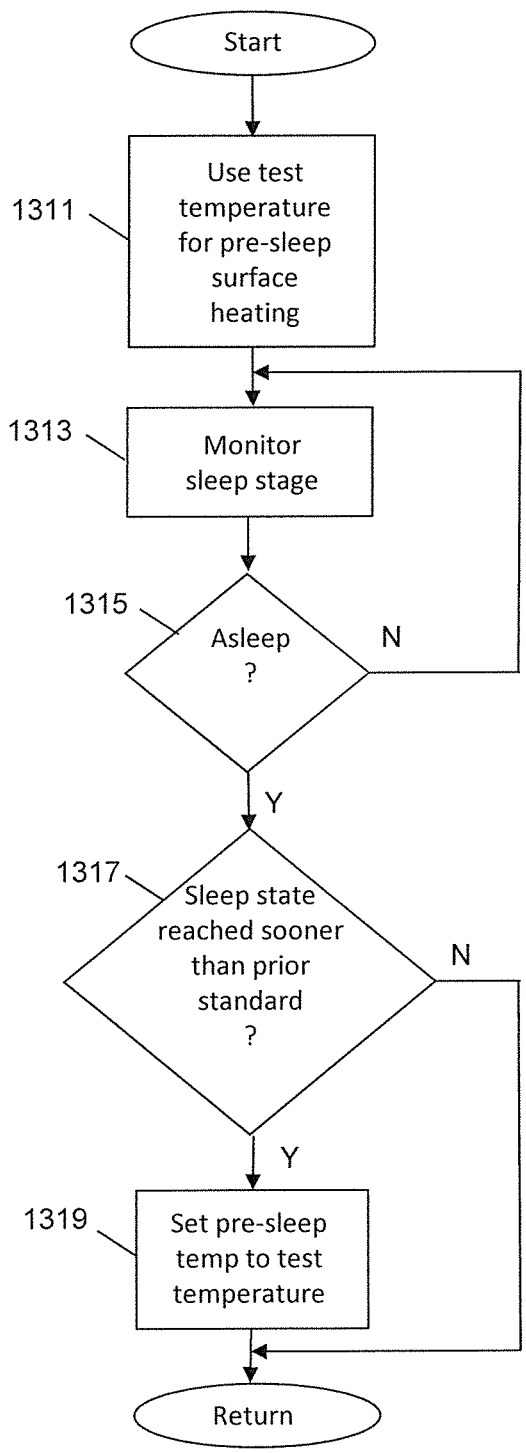
FIG. 13 is a flow diagram of a process for determining a temperature of a sleep surface for a pre-sleep time in accordance with aspects of the invention.

FIG. 13 is a flow diagram of a process for determining a temperature of a sleep surface for a pre-sleep time in accordance with aspects of the invention. In some embodiments the process is performed by a bed with a heating and/or cooling component. In some embodiments the process is performed by a controller of a bed with a heating and/or cooling component. In some embodiments the process is performed by a controller, which may be a processor and in other embodiments, this computation is performed on a remote server coupled to the controller over a network. In some embodiments the processor receives information indicative of one or more temperatures of, or proximate, a sleep surface of a bed. In some embodiments the processor receives information from a pressure sensor indicating pressure on at least a portion of the sleep surface, and in some embodiments the processor receives information from biometric sensors of the bed, or associated with a user of the bed.

In block 1311 the process commands temperature of the sleep surface to a test temperature, as part of conditioning the bed for sleep by a user. In some embodiments the process does so at a time indicated as a preset sleep surface time, for example as determined in block 811 of the process of FIG. 8. In some embodiments the test temperature is a temperature different than a temperature the process generally uses for preconditioning the bed for sleep by the user, a temperature that may be the first temperature discussed elsewhere herein. In some embodiments the some test temperature is three to five degrees, or up to five degrees, Fahrenheit cooler, or warmer, than, the first temperature. In some embodiments the test temperature is provided to the bed by a remote server. In some embodiments the test temperature is determined based on information regarding other sleepers.

In block 1313 the process monitors sleep stages of the user. In some embodiments the process monitors whether the user is asleep. In some embodiments the process monitors whether the user is asleep by determining if the user is in the bed, for example using a pressure sensor or motion sensor. In some embodiments the process determines if the user is asleep by determining if motion patterns, or lack thereof, of the user in the bed matches a pattern indicating sleep, with the motion patterns sensed by pressure and/or motion sensor. In some embodiments the process detects sleep stages of the user using biometric sensors. In some embodiments the sleep stages of the user include a light sleep stage, for example sleep stages N1 and N2, deep or slow wave sleep stages, for example stages N3 and N4, and a REM sleep stage, with a lack of a sleep stage indicating wakefulness on the part of the user.

In block 1315 the process determines if the user has fallen asleep. If not, the process continues monitoring sleep stages of the user in block 1313. Otherwise the process continues to block 1317.

In block 1317 the process determines if the user fell asleep faster with the sleep surface commanded to the test temperature than with the first temperature. In some embodiments the process may perform the operations of blocks 1311-1315 multiple times across multiple nights, and use an average, or some other statistically calculated value, for determining whether the user fell asleep faster with the sleep surface commanded to the test temperature than with the sleep surface commanded to the first temperature.

If the process determines that the user fell asleep faster, in response the process changes the first temperature, the temperature for use in preconditioning the bed for sleep by the user, to the test temperature in block 1319. In some embodiments the process does so by setting a value or values in memory indicative of the test temperature.

The process thereafter returns.

Although the invention has been discussed with respect to various embodiments, it should be recognized that the invention comprises the novel and non-obvious claims supported by this disclosure.

What is claimed is:

1. A method for conditioning a sleep environment, comprising:
   receiving an indication that a user is on a sleep surface;
   after receiving the indication that the user is on the sleep surface, setting at least a portion of the sleep surface to a first temperature for a first period of time, the first period of time being less than a total period of time the user is expected to be asleep on the sleep surface during a sleep session;

wherein the setting of the at least the portion of the sleep surface to the first temperature occurs after receiving an indication that the user is asleep on the sleep surface;

wherein the indication that the user is asleep on the sleep surface is based on information from biometric sensors;

wherein the method further comprises determining sleep stages of the user through processing of information from the biometric sensors;

wherein the first period of time concludes at a time the determined sleep stage of the user is a REM-dominant sleep stage;

wherein the method further comprises:
  determining an amount of time the user experienced slow wave sleep stages during the first period of time;
  for a subsequent sleep session, receiving a further indication that that the user is asleep on the sleep surface, and, after receiving the further indication that the user is asleep on the sleep surface, setting the portion of the sleep surface to a second temperature for the first period of time during the subsequent sleep session;
  determining an amount of time the user experienced slow wave sleep stages during the first period of time of the subsequent sleep session;
  determining that amount of time the user experienced slow wave sleep stages during the first period of time of the subsequent sleep session is longer than the amount of time the user experienced slow wave sleep stages during the first period of time; and
  in response to determining that the amount of time the user experienced slow wave sleep stages during the first period of time of the subsequent sleep session is longer than the amount of time the user experienced slow wave sleep stages during the first period of time, setting the portion of the sleep surface to the second temperature during the first period of time during further subsequent sleep sessions.

2. The method of claim 1, wherein the first temperature is lower than a stable temperature of the sleep surface after the user is on the sleep surface and before the at least a portion of the sleep surface is set to the first temperature.

3. The method of claim 1, wherein the first temperature is lower than a temperature at the sleep surface at a time of receipt of the indication that the user is asleep on the sleep surface.

4. A method for conditioning a sleep environment, comprising:
  receiving an indication that a user is on a sleep surface;
  after receiving the indication that the user is on the sleep surface, setting at least a portion of the sleep surface to a first temperature for a first period of time, the first period of time being less than a total period of time the user is expected to be asleep on the sleep surface during a sleep session;
  wherein the setting of the at least the portion of the sleep surface to the first temperature occurs after receiving an indication that the user is asleep on the sleep surface;
  wherein the indication that the user is asleep on the sleep surface is based on information from biometric sensors;
  wherein the method further comprises determining sleep stages of the user through processing of information from the biometric sensors;
  wherein the first period of time concludes at a time the determined sleep stage of the user is a REM-dominant sleep stage;
  wherein the first temperature is based on a stored first value indicating the first temperature, and the method further comprises:
    storing an indication of amount of time for which the user is in a slow wave sleep stage during the first period of time;
    subsequently setting the portion of the sleep surface to a different temperature, for at least a second period of time;
    determining that an amount of time the user is in a slow wave sleep stage in the second period of time with the sleep surface set to the different temperature is greater than the amount of time the user is in the slow wave sleep stage during the first period of time; and
    in response to the determination regarding the amounts of time the user is in the slow wave sleep stage, setting the first value to a value reflecting the different temperature.

5. The method of claim 4, wherein the subsequently setting the portion of the sleep surface to the different temperature occurs during a subsequent sleep session to the setting the portion of the sleep surface to the first temperature.

6. The method of claim 4, further comprising, for a time after setting the first value to the value reflecting the different temperature, receiving a further indication that that the user is asleep on the sleep surface, and, after receiving the further indication that the user is asleep on the sleep surface, setting the portion of the sleep surface to the different temperature.

7. The method of claim 4, wherein the different temperature is up to 5 degrees Fahrenheit below the first temperature.

8. The method of claim 1, further comprising setting the portion of the sleep surface to a third temperature prior to a time the user is expected to sleep on the sleep surface, wherein the third temperature is greater than the first temperature.

9. The method of claim 1, wherein the portion of the sleep surface is set to the first temperature by heating or cooling the sleep surface.

10. The method of claim 9, wherein the heating or cooling of the sleep surface is performed using a thermoelectric device.

11. A method for conditioning a sleep environment, comprising:
  receiving an indication that a user is on a sleep surface;
  after receiving the indication that the user is on the sleep surface, setting at least a portion of the sleep surface to a first temperature for a first period of time, the first period of time being less than a total period of time the user is expected to be asleep on the sleep surface during a sleep session;
  wherein the setting of the at least the portion of the sleep surface to the first temperature occurs after receiving an indication that the user is asleep on the sleep surface;
  wherein the method further comprises:
    setting the portion of the sleep surface to a second temperature at a time the user is asleep, wherein the portion of the sleep surface is set to the second temperature a predetermined time before the user is expected to be awake;
    for a subsequent sleep session, setting the portion of the sleep surface to a different temperature instead of the second temperature at the predetermined time before the user is expected to be awake from the subsequent sleep session;

determining that the user awakes closer to the expected wake time for the subsequent sleep session than for the prior sleep session; and in response to the determination, setting the portion of the sleep surface to the different temperature at the predetermined times before the user is expected to be awake for further subsequent sleep sessions.

12. A method for conditioning a sleep environment, comprising:

receiving an indication that a user is on a sleep surface;

after receiving the indication that the user is on the sleep surface, setting at least a portion of the sleep surface to a first temperature for a first period of time, the first period of time being less than a total period of time the user is expected to be asleep on the sleep surface during a sleep session;

wherein the setting of the at least the portion of the sleep surface to the first temperature occurs after receiving an indication that the user is asleep on the sleep surface;

wherein the method further comprises:

setting the portion of the sleep surface to a second temperature at a time the user is asleep, wherein the portion of the sleep surface is set to the second temperature a predetermined time before the user is expected to be awake;

for a subsequent sleep session, setting the portion of the sleep surface to the second temperature at a time different than the predetermined time before the user is expected to be awake from the subsequent sleep session;

determining that the user awakes closer to the expected wake time for the subsequent sleep session than for the prior sleep session; and in response to the determination, setting the portion of the sleep surface to the second temperature at the time different than the predetermined time before the user is expected to be awake for further subsequent sleep sessions.

13. A bed, comprising:

an adjustable temperature sleep surface;

a controller configured to command adjustment of temperature of the sleep surface based on information regarding a user of the sleep surface; and biometric sensors coupled to the controller, wherein the controller is further configured to determine sleep stages of the user;

wherein the controller is configured to:

command adjustment of temperature of the sleep surface to a first temperature based on a sleep stage of the user indicating that the user is asleep;

cease commanding adjustment of the temperature of the sleep surface to the first temperature after the user has completed a predetermined number of sleep cycles;

determine the amount of time during which the user experienced slow wave sleep stages during the predetermined number of sleep cycles;

command the temperature of the sleep surface during the predetermined number of sleep cycles for a subsequent sleep session to a temperature different than the first temperature;

determine the amount of time during which the user experienced slow wave sleep stages during the predetermined number of sleep cycles with the sleep surface temperature different than the first temperature; and to change a value for the first temperature to the temperature different than the first temperature if the user experienced a longer period of time in slow wave sleep stages during the predetermined number of sleep cycles with the temperature different than the first temperature.

14. A bed, comprising:

an adjustable temperature sleep surface;

a controller configured to command adjustment of temperature of the sleep surface based on information regarding a user of the sleep surface; and biometric sensors coupled to the controller, wherein the controller is further configured to determine sleep stages of the user;

wherein the controller is configured to:

command adjustment of temperature of the sleep surface to a first temperature based on a sleep stage of the user indicating that the user is asleep;

cease commanding adjustment of the temperature of the sleep surface to the first temperature after the user has completed a predetermined number of sleep cycles;

determine the amount of time during which the user experienced slow wave sleep stages during the predetermined number of sleep cycles;

receive from a remote server a temperature value different than the first temperature;

command the temperature of the sleep surface during the predetermined number of sleep cycles for a subsequent sleep session to the temperature value different than the first temperature;

determine the amount of time during which the user experienced slow wave sleep stages during the predetermined number of sleep cycles with the sleep surface temperature different than the first temperature;

provide information of the amounts of time to the remote server; and receive a new value for use as the first temperature from the remote server.

15. A bed, comprising:

an adjustable temperature sleep surface;

a controller configured to command adjustment of temperature of the sleep surface based on information regarding a user of the sleep surface; and biometric sensors coupled to the controller, wherein the controller is further configured to determine sleep stages of the user;

wherein the controller is configured to:

command adjustment of temperature of the sleep surface to a first temperature based on a sleep stage of the user indicating that the user is asleep;

cease commanding adjustment of the temperature of the sleep surface to the first temperature after the user has completed a predetermined number of sleep cycles;

wherein the controller is further configured to, iteratively:

determine a period of time during which the user experienced slow wave sleep stages, command the temperature of the sleep surface during the predetermined number of sleep cycles for at least one subsequent sleep session to a temperature different than the first temperature, determine if the user experienced a longer period of time at slow wave sleep stages during the at least one subsequent sleep session with the sleep surface temperature different than the first temperature, and change a value for the first temperature to the temperature different than the first temperature if the user experienced a longer period of time in slow wave sleep stages during the at least one subsequent sleep session with the temperature different than the first temperature.

16. The bed of claim 13, further comprising a thermoelectric device coupled to the controller, the thermoelectric device configured for heating or cooling air or fluid to be provided to the adjustable temperature sleep surface.

17. The method of claim 4, wherein the first temperature is lower than a stable temperature of the sleep surface after the user is on the sleep surface and before the at least a portion of the sleep surface is set to the first temperature.

18. The method of claim 4, wherein the first temperature is lower than a temperature at the sleep surface at a time of receipt of the indication that the user is asleep on the sleep surface.

19. The method of claim 4, further comprising setting the portion of the sleep surface to a third temperature prior to a time the user is expected to sleep on the sleep surface, wherein the third temperature is greater than the first temperature.

20. The method of claim 4, wherein the portion of the sleep surface is set to the first temperature by heating or cooling the sleep surface.

21. The method of claim 20, wherein the heating or cooling of the sleep surface is performed using a thermoelectric device.

22. The method of claim 11, wherein the predetermined time before the user is expected to be awake is longer than the time for the sleep surface to reach the second temperature, such that the second temperature is reached before the user is expected to be awake.

23. The method of claim 11, further comprising:
determining that a sleep stage of the user was not a lightest sleep stage immediately prior to awakening; and
in response to the determination, setting the predetermined time to an earlier time for subsequent sleep sessions.

24. The method of claim 11, further comprising:
determining that a sleep stage of the user was not a lightest sleep stage immediately prior to awakening; and
in response to the determination, setting the second temperature with a temperature higher than the second temperature for subsequent sleep sessions.

25. The method of claim 12, wherein the predetermined time before the user is expected to be awake is longer than the time for the sleep surface to reach the second temperature, such that the second temperature is reached before the user is expected to be awake.

26. The method of claim 12, further comprising:
determining that a sleep stage of the user was not a lightest sleep stage immediately prior to awakening; and
in response to the determination, setting the predetermined time to an earlier time for subsequent sleep sessions.

27. The method of claim 12, further comprising:
determining that a sleep stage of the user was not a lightest sleep stage immediately prior to awakening; and
in response to the determination, setting the second temperature with a temperature higher than the second temperature for subsequent sleep sessions.

28. The bed of claim 14, further comprising a thermoelectric device coupled to the controller, the thermoelectric device configured for heating or cooling air or fluid to be provided to the adjustable temperature sleep surface.

29. The bed of claim 15, further comprising a thermoelectric device coupled to the controller, the thermoelectric device configured for heating or cooling air or fluid to be provided to the adjustable temperature sleep surface.

* * * * *